United States Patent
Sack et al.

(10) Patent No.: US 9,545,283 B2
(45) Date of Patent: Jan. 17, 2017

(54) DEVICES AND METHODS FOR PREPARATION OF VERTEBRAL MEMBERS

(71) Applicant: JMEA Corporation, Rockville, MD (US)

(72) Inventors: James A. Sack, Elverson, PA (US); Jack Y. Yeh, North Potomac, MD (US); Sanjog Kumar Mathur, Columbia, MD (US)

(73) Assignee: JMEA Corporation, Rockville, MD (US)

( * ) Notice: Subject to any disclaimer, the term of this patent is extended or adjusted under 35 U.S.C. 154(b) by 0 days.

(21) Appl. No.: 14/576,492

(22) Filed: Dec. 19, 2014

(65) Prior Publication Data

US 2015/0173808 A1    Jun. 25, 2015

Related U.S. Application Data

(60) Provisional application No. 61/919,994, filed on Dec. 23, 2013.

(51) Int. Cl.
*A61B 17/58* (2006.01)
*A61B 17/60* (2006.01)
(Continued)

(52) U.S. Cl.
CPC ......... *A61B 17/885* (2013.01); *A61B 17/1671* (2013.01); *A61B 2017/00261* (2013.01)

(58) Field of Classification Search
CPC .............. A61B 17/025; A61B 2017/0256; A61F 2/4611
(Continued)

(56) References Cited

U.S. PATENT DOCUMENTS 2,655,154 A * 10/1953 Richter .................. 606/159
3,667,474 A *  6/1972 Lapkin et al. ........... 606/198
(Continued)

FOREIGN PATENT DOCUMENTS

EP    0464463 A1   1/1992

OTHER PUBLICATIONS

International Search Report and the Written Opinion mailed May 1, 2015 in International Patent Application No. PCT/US2014/071796.

*Primary Examiner* — Eduardo C Robert
*Assistant Examiner* — Michelle C Eckman
(74) *Attorney, Agent, or Firm* — Plumsea Law Group, LLC

(57) ABSTRACT

Devices and methods for preparing a surgical site, and in particular vertebral members, which may include a retractable tool and an actuator. The tool may include distal and proximal members. A distal side of the distal member may be fixed in a longitudinal direction and pivotable at a point of rotation. A proximal side of the proximal member may be pivotably connected to the actuator. In a retracted position, the distal member may be pivotably connected to the proximal member longitudinally in between the point of rotation and the proximal side of the proximal member. Moving the actuator in a distal direction may push the proximal member and the distal member such that the proximal member pivots with respect to the actuator and distal member, the distal member pivots with respect to the proximal member and point of rotation, and the proximal member and distal member move laterally outward.

26 Claims, 32 Drawing Sheets

(51) Int. Cl.
*A61F 2/00* (2006.01)
*A61B 17/88* (2006.01)
*A61B 17/16* (2006.01)
*A61B 17/00* (2006.01)

(58) Field of Classification Search
USPC ............... 606/86 A, 99, 105; 623/17.15
See application file for complete search history.

(56) References Cited

U.S. PATENT DOCUMENTS

| | | | | |
|---|---|---|---|---|
| 3,704,711 | A * | 12/1972 | Park ........................... | 604/284 |
| 5,069,679 | A * | 12/1991 | Taheri ......................... | 606/159 |
| 5,074,871 | A * | 12/1991 | Groshong ................... | 606/170 |
| 5,113,846 | A * | 5/1992 | Hiltebrandt et al. ......... | 600/225 |
| 5,178,133 | A * | 1/1993 | Pena ............................ | 600/203 |
| 5,195,505 | A * | 3/1993 | Josefsen ...................... | 600/204 |
| 5,199,419 | A * | 4/1993 | Remiszewski et al. ...... | 600/204 |
| 5,235,966 | A * | 8/1993 | Jamner ......................... | 600/204 |
| 5,325,848 | A * | 7/1994 | Adams et al. ................ | 600/206 |
| 5,351,679 | A * | 10/1994 | Mayzels et al. .............. | 600/214 |
| 5,358,496 | A * | 10/1994 | Ortiz et al. ................... | 606/198 |
| 5,403,343 | A * | 4/1995 | Sugarbaker ................... | 606/207 |
| 5,451,204 | A * | 9/1995 | Yoon ............................. | 604/1 |
| 5,549,636 | A * | 8/1996 | Li .................................. | 606/206 |
| 5,613,950 | A * | 3/1997 | Yoon ............................. | 604/105 |
| 5,662,676 | A * | 9/1997 | Koninckx ..................... | 606/198 |
| 5,681,349 | A * | 10/1997 | Sugarbaker ................... | 606/207 |
| 5,755,661 | A * | 5/1998 | Schwartzman ............... | 600/216 |
| 5,891,162 | A * | 4/1999 | Sugarbaker et al. ......... | 606/207 |
| 6,039,761 | A * | 3/2000 | Li et al. ........................ | 623/17.16 |
| 6,582,451 | B1 * | 6/2003 | Marucci et al. .............. | 606/207 |
| 6,676,665 | B2 * | 1/2004 | Foley et al. .................. | 606/105 |
| 6,840,944 | B2 * | 1/2005 | Suddaby ....................... | 606/105 |
| 7,114,501 | B2 * | 10/2006 | Johnson et al. .............. | 128/877 |
| 7,442,195 | B1 * | 10/2008 | Behrens ....................... | 606/86 A |
| 7,445,598 | B2 * | 11/2008 | Orban, III ..................... | 600/210 |
| 7,559,930 | B2 * | 7/2009 | Allard et al. ................. | 606/86 A |
| 7,740,578 | B2 * | 6/2010 | Little ............................ | 600/117 |
| 7,901,409 | B2 * | 3/2011 | Canaveral et al. .......... | 606/86 R |
| 7,922,767 | B2 | 4/2011 | Sack et al. | |
| 8,197,548 | B2 | 6/2012 | Sack et al. | |
| 8,328,818 | B1 * | 12/2012 | Seifert et al. ................. | 606/105 |
| 8,353,911 | B2 * | 1/2013 | Goldin et al. ................ | 606/79 |
| 8,454,584 | B2 * | 6/2013 | Ducharme .................... | 606/1 |
| 8,486,138 | B2 * | 7/2013 | Vesely .......................... | 623/2.11 |
| 8,998,992 | B2 * | 4/2015 | Seifert et al. ................. | 623/17.16 |
| 9,138,563 | B2 | 9/2015 | Glenn | |
| 2003/0105467 | A1 * | 6/2003 | Ralph et al. .................. | 606/90 |
| 2003/0220650 | A1 * | 11/2003 | Major et al. .................. | 606/90 |
| 2003/0236520 | A1 * | 12/2003 | Lim et al. ..................... | 606/61 |
| 2004/0059362 | A1 * | 3/2004 | Knodel et al. ............... | 606/167 |
| 2004/0087947 | A1 * | 5/2004 | Lim et al. ..................... | 606/61 |
| 2004/0102774 | A1 * | 5/2004 | Trieu ............................ | 606/61 |
| 2004/0193158 | A1 * | 9/2004 | Lim et al. ..................... | 606/61 |
| 2004/0215197 | A1 * | 10/2004 | Smith et al. .................. | 606/79 |
| 2005/0080425 | A1 * | 4/2005 | Bhatnagar et al. ........... | 606/90 |
| 2005/0124989 | A1 * | 6/2005 | Suddaby ....................... | 606/53 |
| 2005/0182416 | A1 * | 8/2005 | Lim et al. ..................... | 606/90 |
| 2005/0182417 | A1 * | 8/2005 | Pagano ......................... | 606/92 |
| 2005/0228391 | A1 * | 10/2005 | Levy et al. ................... | 606/86 |
| 2005/0261683 | A1 * | 11/2005 | Veldhuizen et al. .......... | 606/61 |
| 2006/0116689 | A1 * | 6/2006 | Albans et al. ................ | 606/92 |
| 2006/0116690 | A1 | 6/2006 | Pagano | |
| 2006/0241643 | A1 * | 10/2006 | Lim et al. ..................... | 606/90 |
| 2007/0032791 | A1 * | 2/2007 | Greenhalgh .................. | 606/61 |
| 2007/0055274 | A1 * | 3/2007 | Appenzeller et al. ........ | 606/90 |
| 2007/0149978 | A1 * | 6/2007 | Shezifi et al. ................ | 606/90 |
| 2007/0260260 | A1 * | 11/2007 | Hahn et al. ................... | 606/102 |
| 2007/0260314 | A1 * | 11/2007 | Biyani .......................... | 623/17.11 |
| 2007/0260315 | A1 * | 11/2007 | Foley et al. .................. | 623/17.12 |
| 2007/0270874 | A1 * | 11/2007 | Anderson ..................... | 606/90 |
| 2008/0058833 | A1 * | 3/2008 | Rizvi ............................ | 606/119 |
| 2008/0114364 | A1 * | 5/2008 | Goldin et al. ................ | 606/79 |
| 2008/0114367 | A1 * | 5/2008 | Meyer .......................... | 606/90 |
| 2008/0177259 | A1 * | 7/2008 | Wu ............................... | 606/57 |
| 2008/0177266 | A1 * | 7/2008 | Metcalf et al. ............... | 606/80 |
| 2008/0243255 | A1 * | 10/2008 | Butler et al. ................. | 623/17.16 |
| 2008/0300636 | A1 * | 12/2008 | Carli et al. ................... | 606/280 |
| 2009/0076607 | A1 * | 3/2009 | Aalsma et al. ............... | 623/17.16 |
| 2009/0157084 | A1 * | 6/2009 | Aalsma et al. ............... | 606/90 |
| 2010/0121453 | A1 * | 5/2010 | Peterman ...................... | 623/17.11 |
| 2010/0130817 | A1 * | 5/2010 | Conlon ......................... | 600/106 |
| 2010/0249785 | A1 * | 9/2010 | Betts ............................. | 606/79 |
| 2011/0015638 | A1 * | 1/2011 | Pischl et al. | |
| 2011/0106186 | A1 * | 5/2011 | Wolfson ....................... | 606/86 R |
| 2012/0071977 | A1 * | 3/2012 | Oglaza et al. ................ | 623/17.11 |
| 2012/0083887 | A1 * | 4/2012 | Purcell et al. ................ | 623/17.16 |
| 2012/0123546 | A1 * | 5/2012 | Medina ........................ | 623/17.16 |
| 2012/0271357 | A1 | 10/2012 | Arthur et al. | |
| 2012/0277864 | A1 * | 11/2012 | Brodke et al. ............... | 623/17.16 |
| 2012/0310048 | A1 * | 12/2012 | Siegal et al. ................. | 600/206 |
| 2013/0018376 | A1 * | 1/2013 | Yoon et al. ................... | 606/79 |
| 2013/0041471 | A1 * | 2/2013 | Siegal et al. ................. | 623/17.16 |
| 2013/0079883 | A1 * | 3/2013 | Butler et al. ................. | 623/17.16 |
| 2013/0116791 | A1 * | 5/2013 | Theofilos ..................... | 623/17.16 |
| 2013/0123927 | A1 * | 5/2013 | Malandain .................... | 623/17.16 |
| 2013/0274558 | A1 * | 10/2013 | Deitch et al. ................. | 600/204 |
| 2013/0274560 | A1 * | 10/2013 | Deitch et al. ................. | 600/219 |
| 2013/0274561 | A1 * | 10/2013 | Deitch et al. ................. | 600/219 |
| 2013/0317301 | A1 * | 11/2013 | Deitch et al. ................. | 600/202 |
| 2013/0325128 | A1 * | 12/2013 | Perloff et al. ................ | 623/17.16 |
| 2014/0025084 | A1 * | 1/2014 | Taylor et al. ................. | 606/119 |
| 2014/0052143 | A1 * | 2/2014 | Deitch et al. ................. | 606/119 |
| 2014/0052253 | A1 * | 2/2014 | Perloff et al. ................ | 623/17.15 |
| 2014/0107424 | A1 * | 4/2014 | Taylor et al. ................. | 600/204 |
| 2014/0188224 | A1 * | 7/2014 | Dmuschewsky .......... | 623/17.16 |
| 2014/0214043 | A1 * | 7/2014 | Lim ............................... | 606/90 |
| 2014/0277185 | A1 * | 9/2014 | Boileau et al. ............... | 606/300 |
| 2014/0277490 | A1 * | 9/2014 | Perloff et al. ................ | 623/17.16 |
| 2014/0343677 | A1 * | 11/2014 | Davis et al. .................. | 623/17.15 |
| 2014/0343678 | A1 * | 11/2014 | Suddaby et al. ............. | 623/17.16 |
| 2015/0012098 | A1 * | 1/2015 | Eastlack et al. .............. | 623/17.15 |
| 2015/0018954 | A1 * | 1/2015 | Loebl et al. .................. | 623/17.16 |
| 2015/0073421 | A1 * | 3/2015 | Siegal et al. ................. | 606/90 |
| 2015/0100128 | A1 * | 4/2015 | Glerum et al. ............... | 623/17.16 |
| 2015/0230786 | A1 * | 8/2015 | Fehling et al. ............... | 606/327 |
| 2015/0230848 | A1 * | 8/2015 | Chirico et al. ............... | 606/90 |
| 2015/0282797 | A1 * | 10/2015 | O'Neil et al. ................ | 606/279 |
| 2015/0282943 | A1 * | 10/2015 | McLean ....................... | 623/17.16 |
| 2015/0342586 | A1 * | 12/2015 | Lim et al. ..................... | 606/90 |
| 2015/0351925 | A1 * | 12/2015 | Emerick et al. ............. | 623/17.16 |

\* cited by examiner

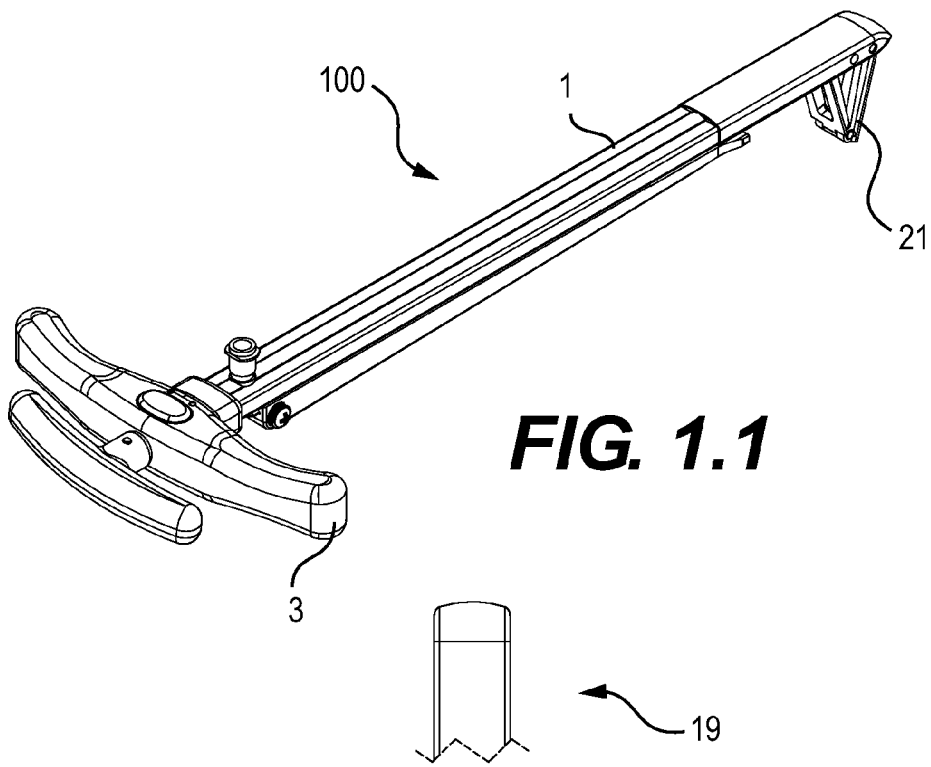
FIG. 1.1
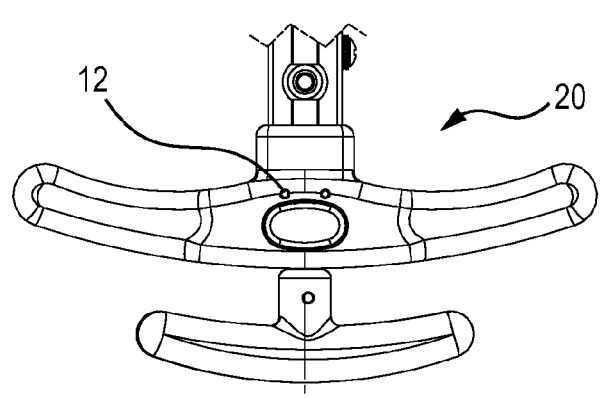
FIG. 1.2
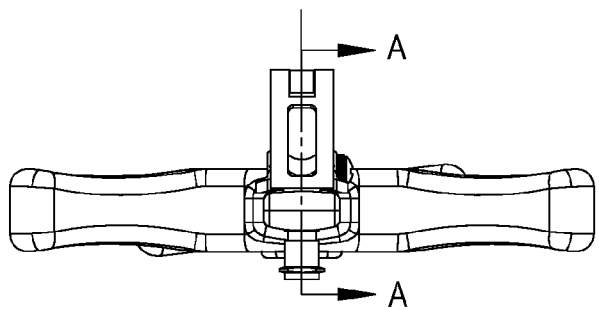
FIG. 1.3

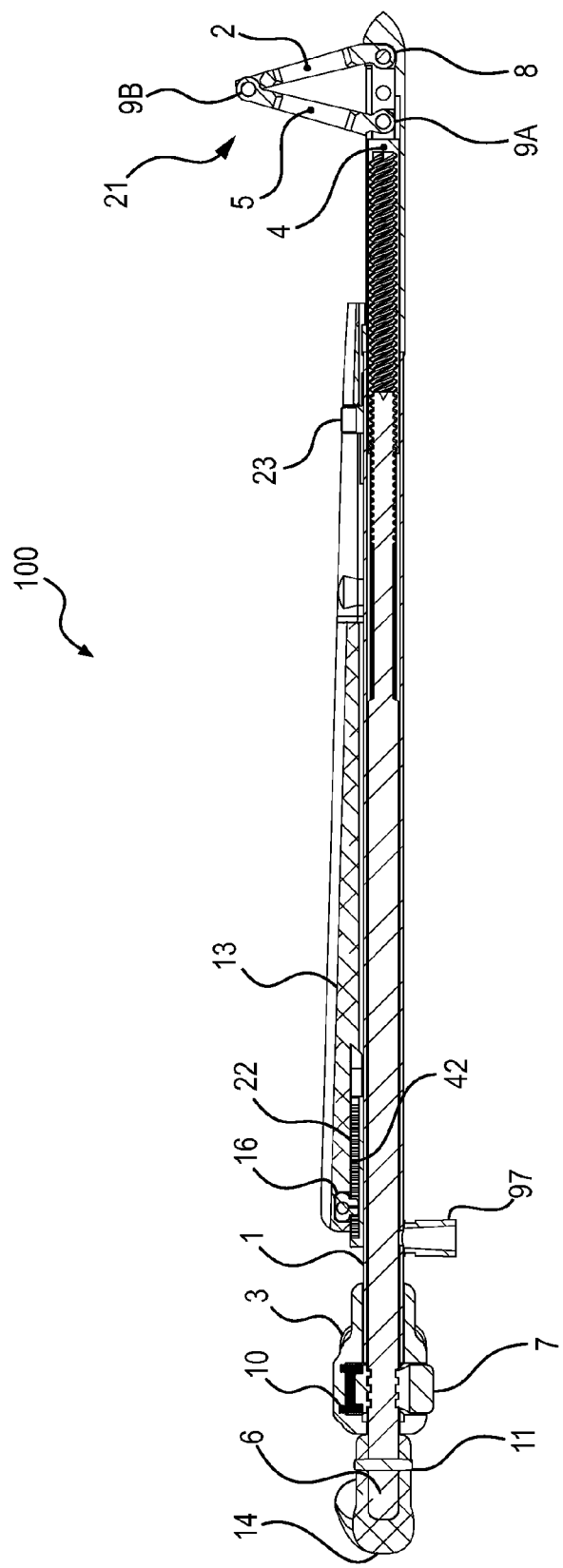
FIG. 1.4

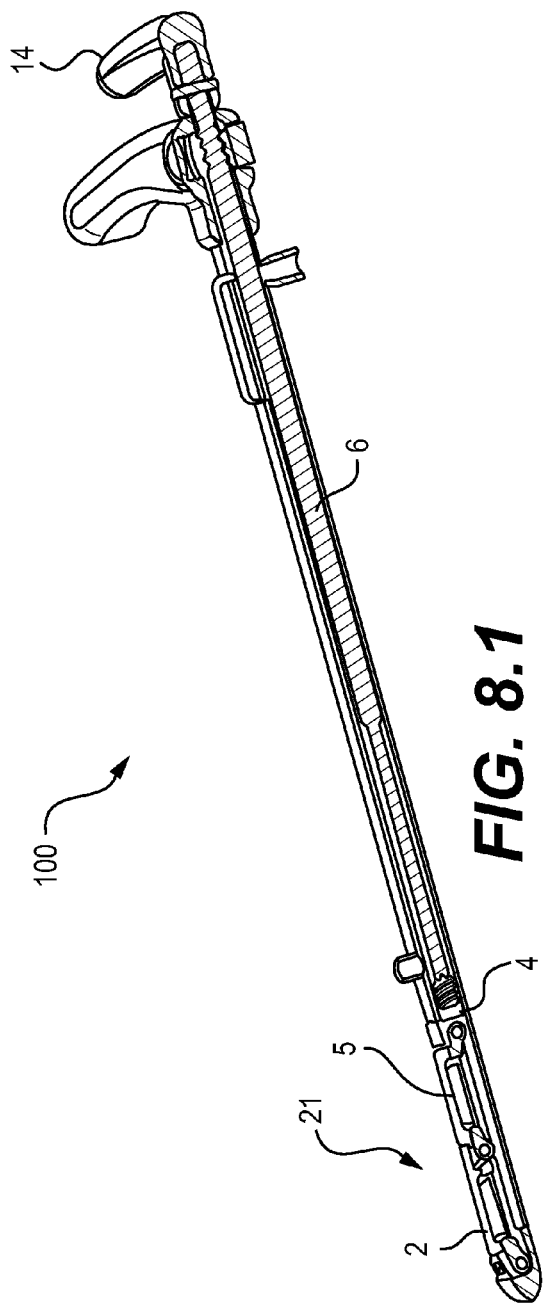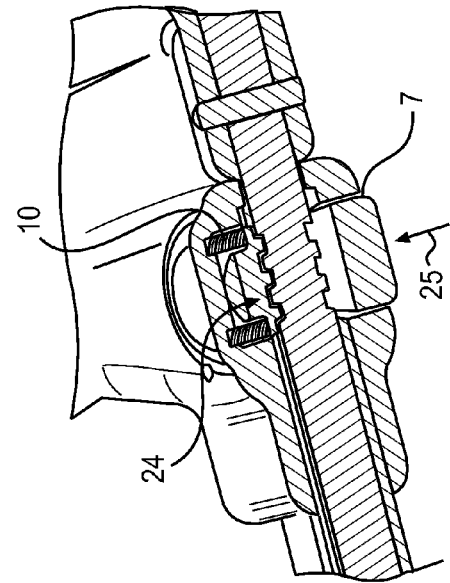

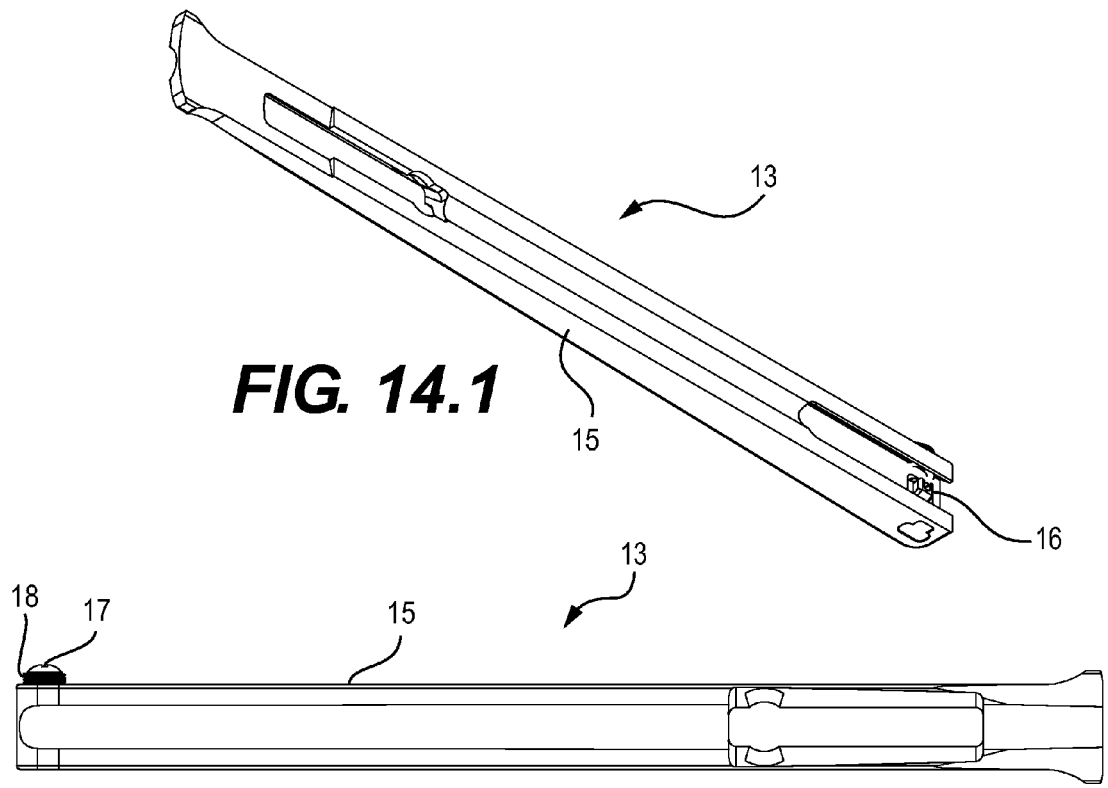
FIG. 14.1
FIG. 14.2
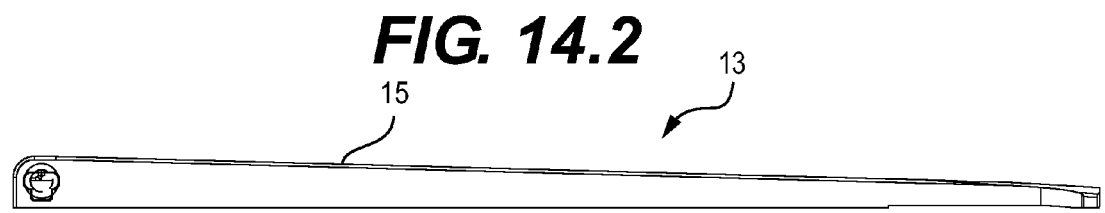
FIG. 14.3
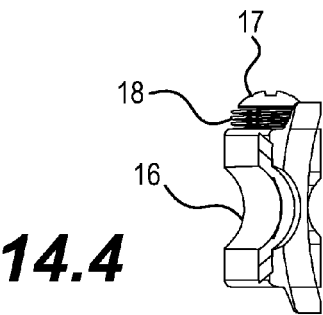
FIG. 14.4

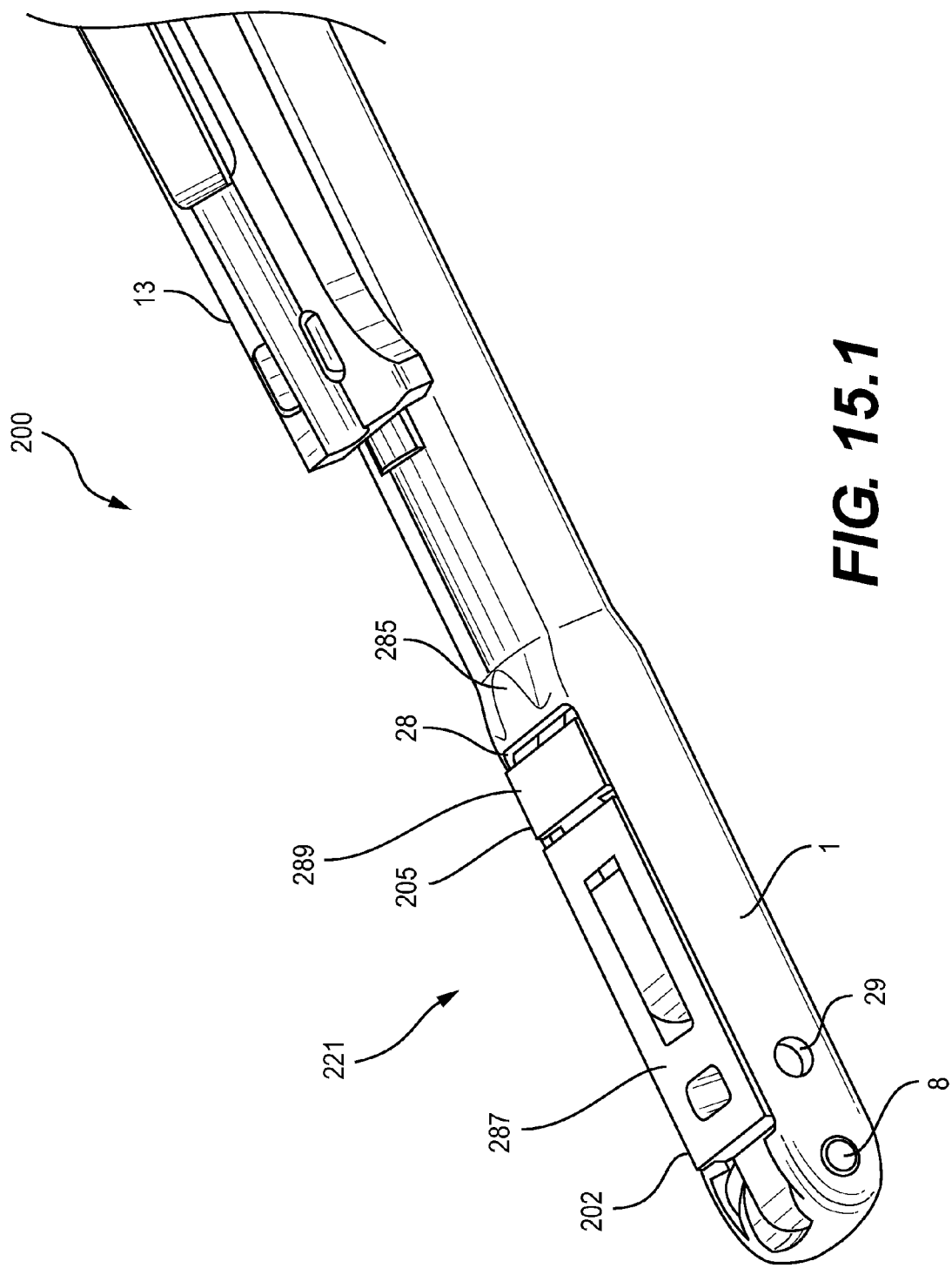
FIG. 15.1

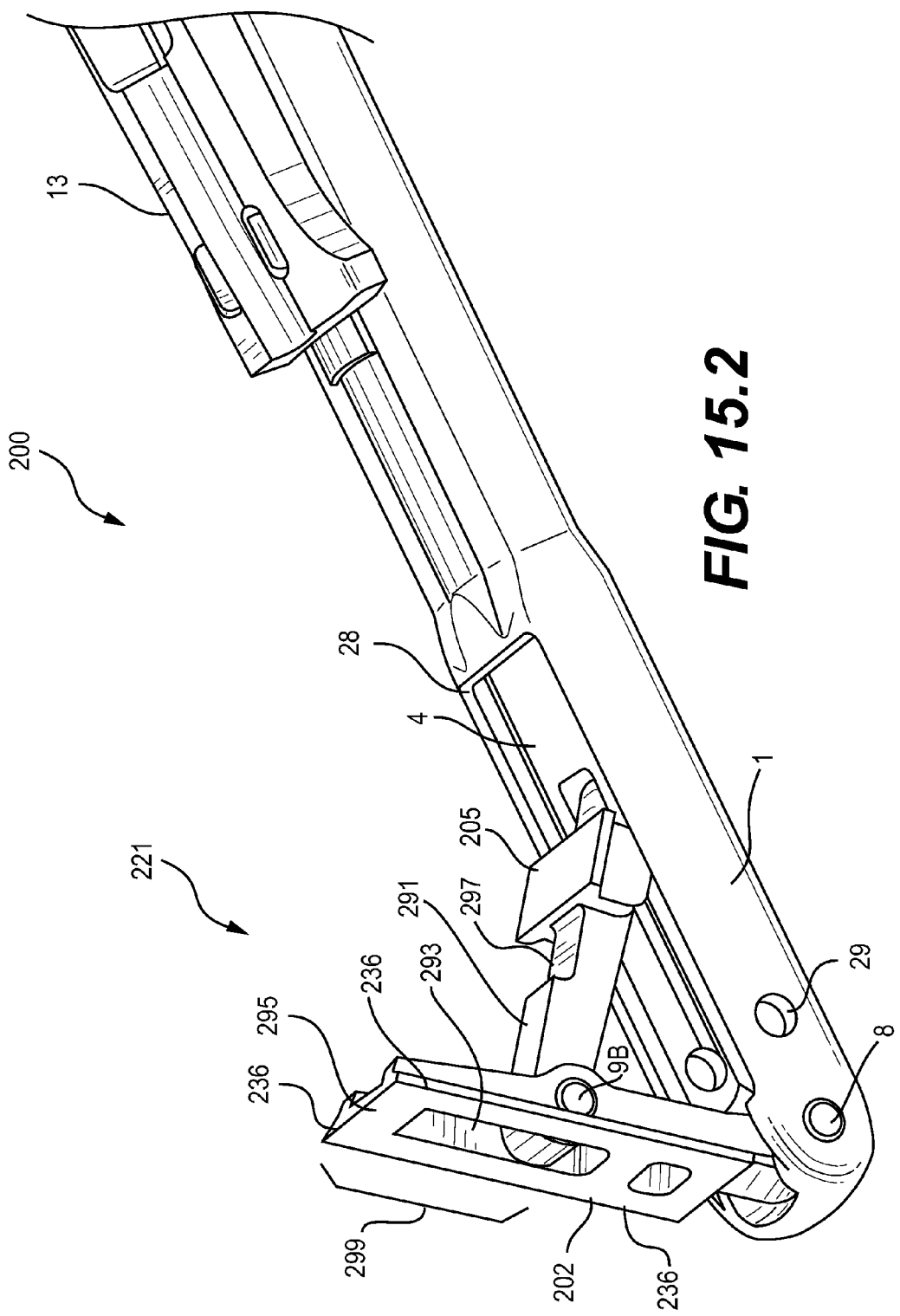
FIG. 15.2

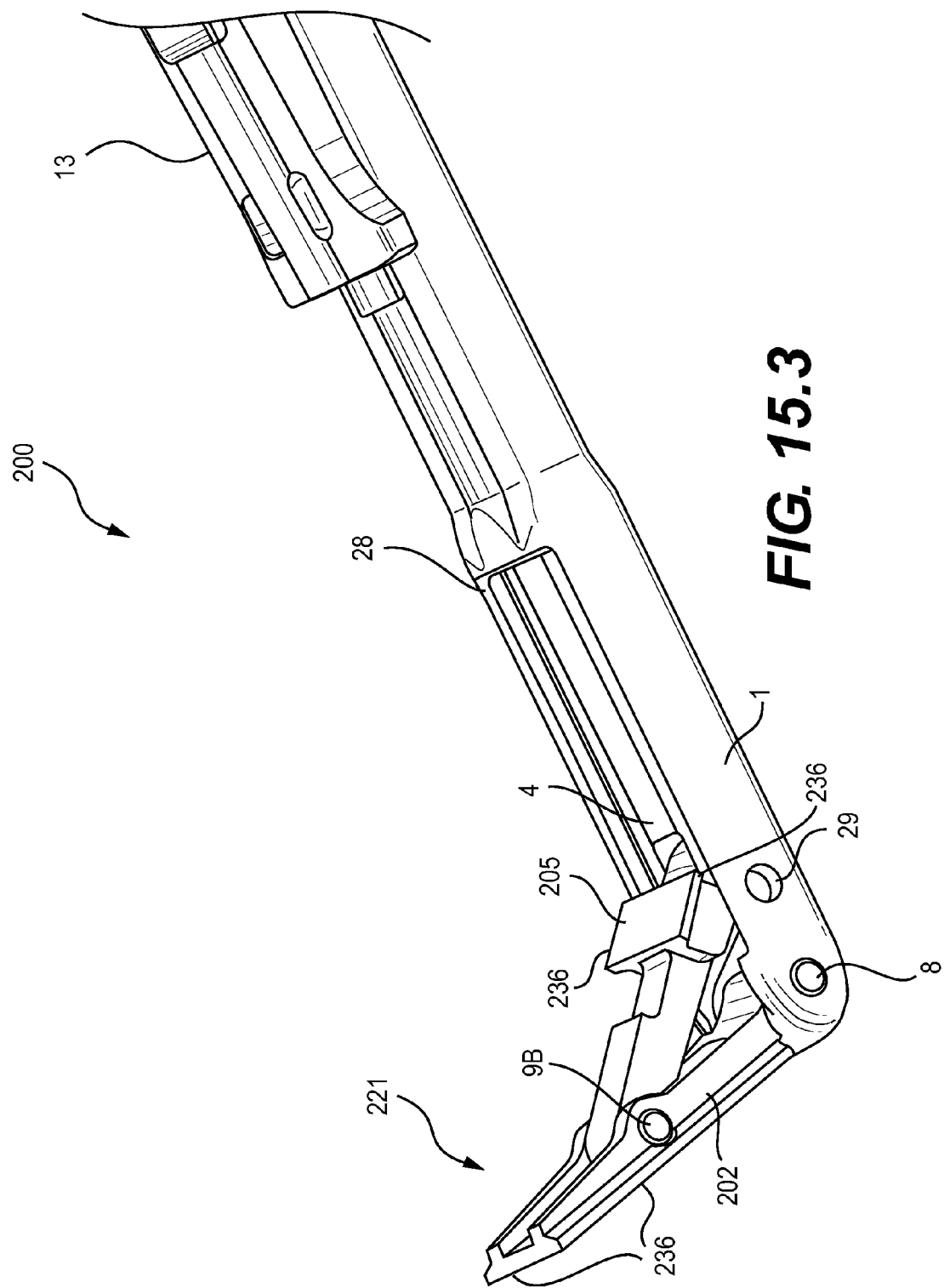

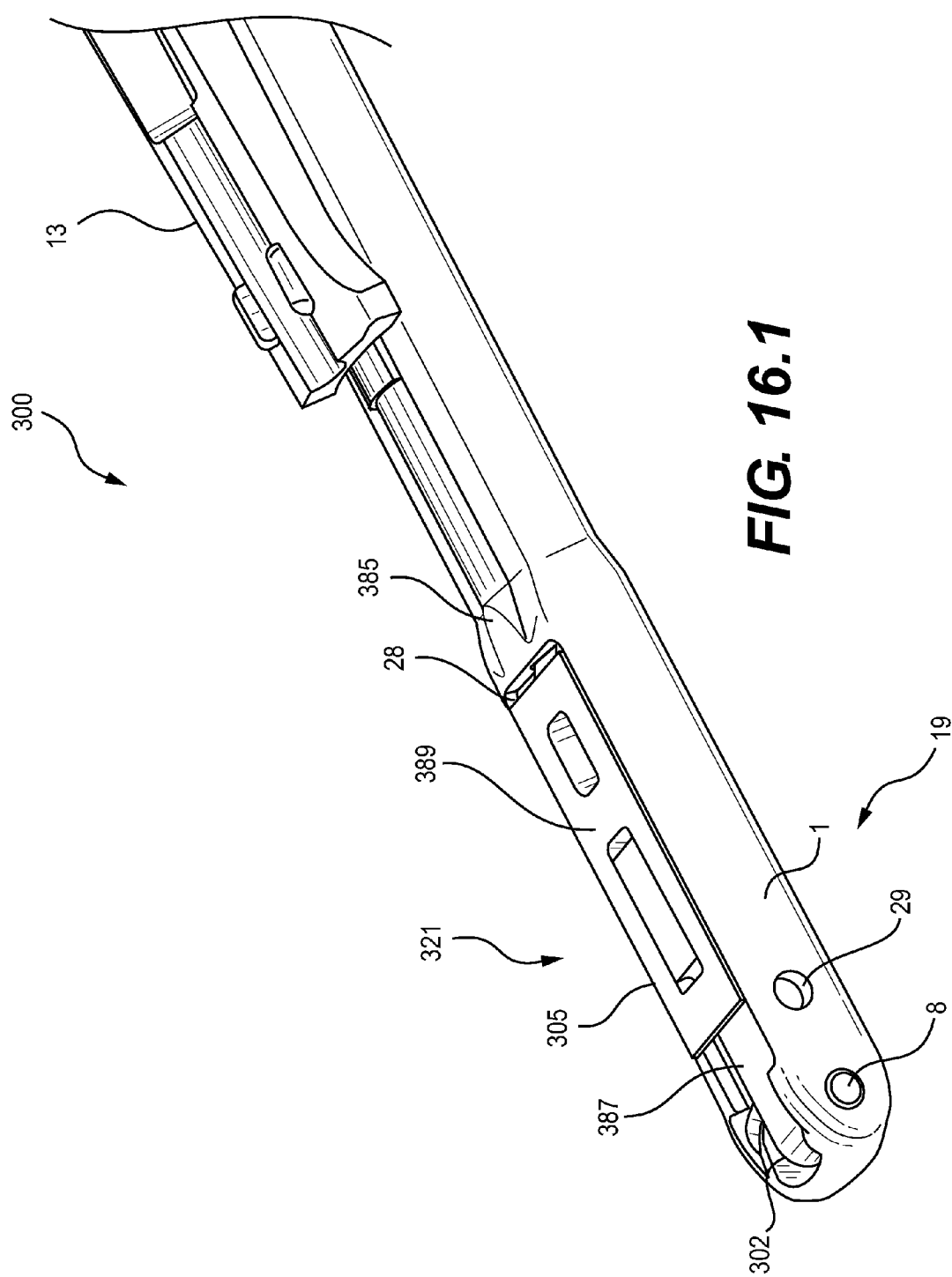
FIG. 16.1

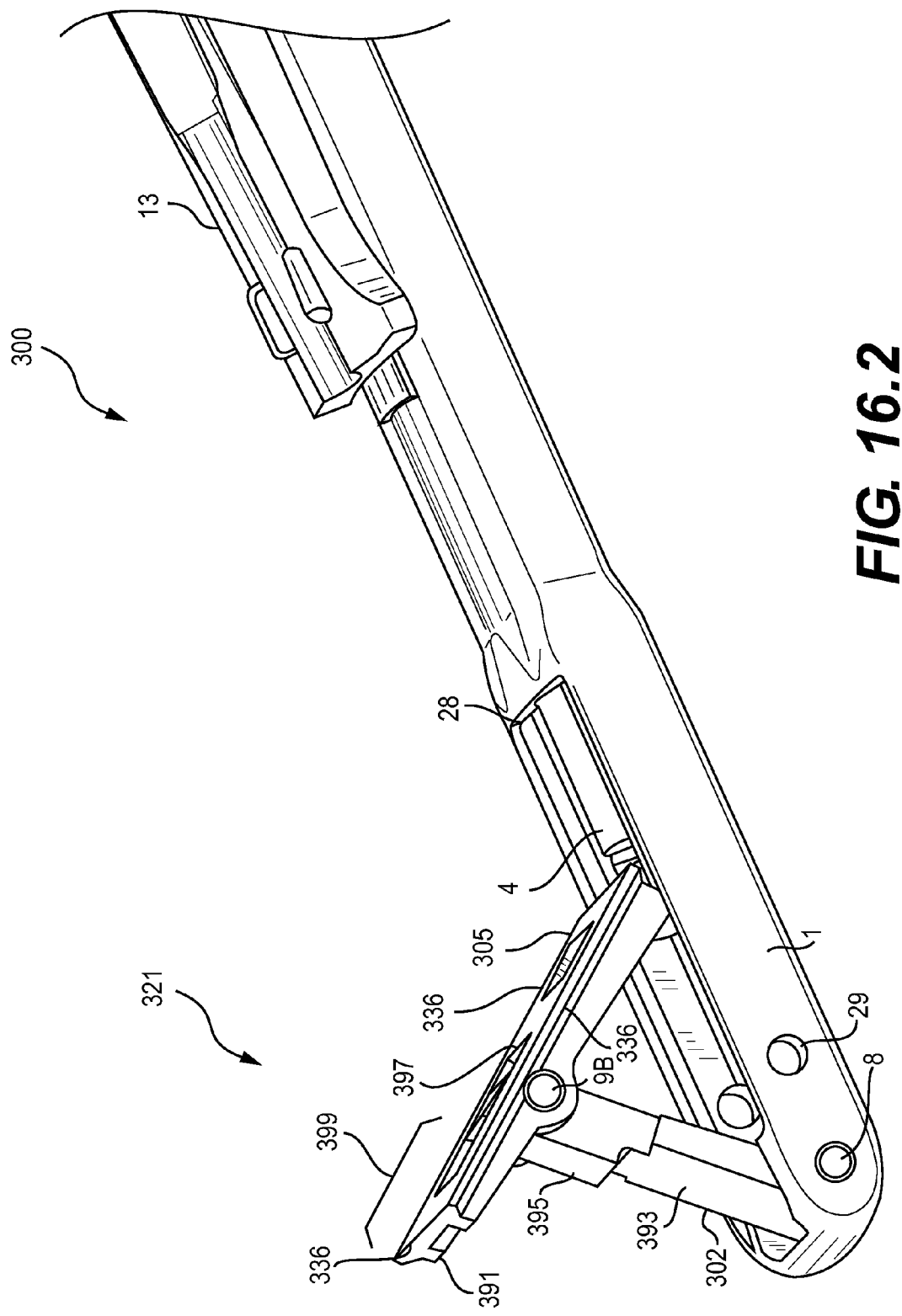
FIG. 16.2

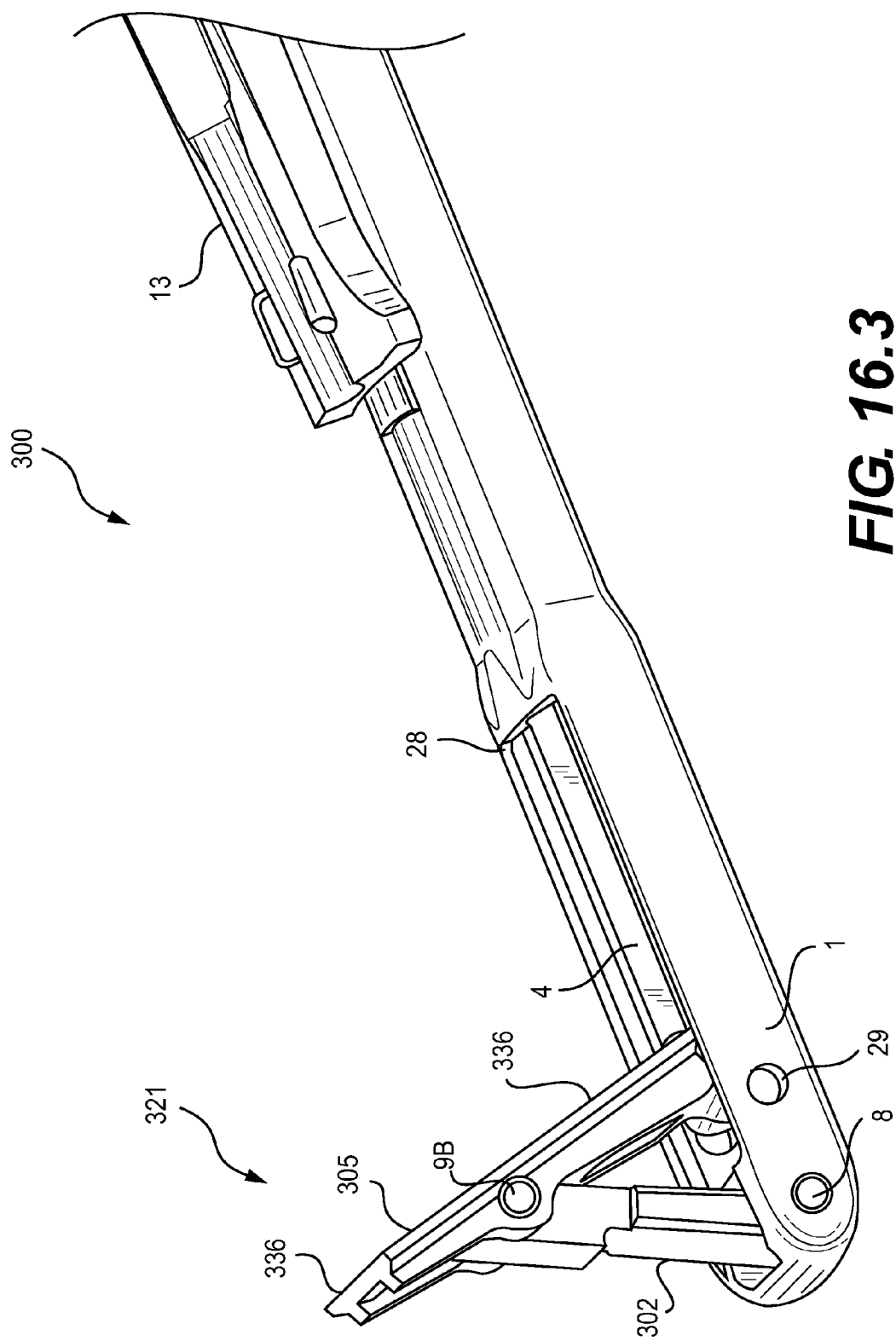
FIG. 16.3

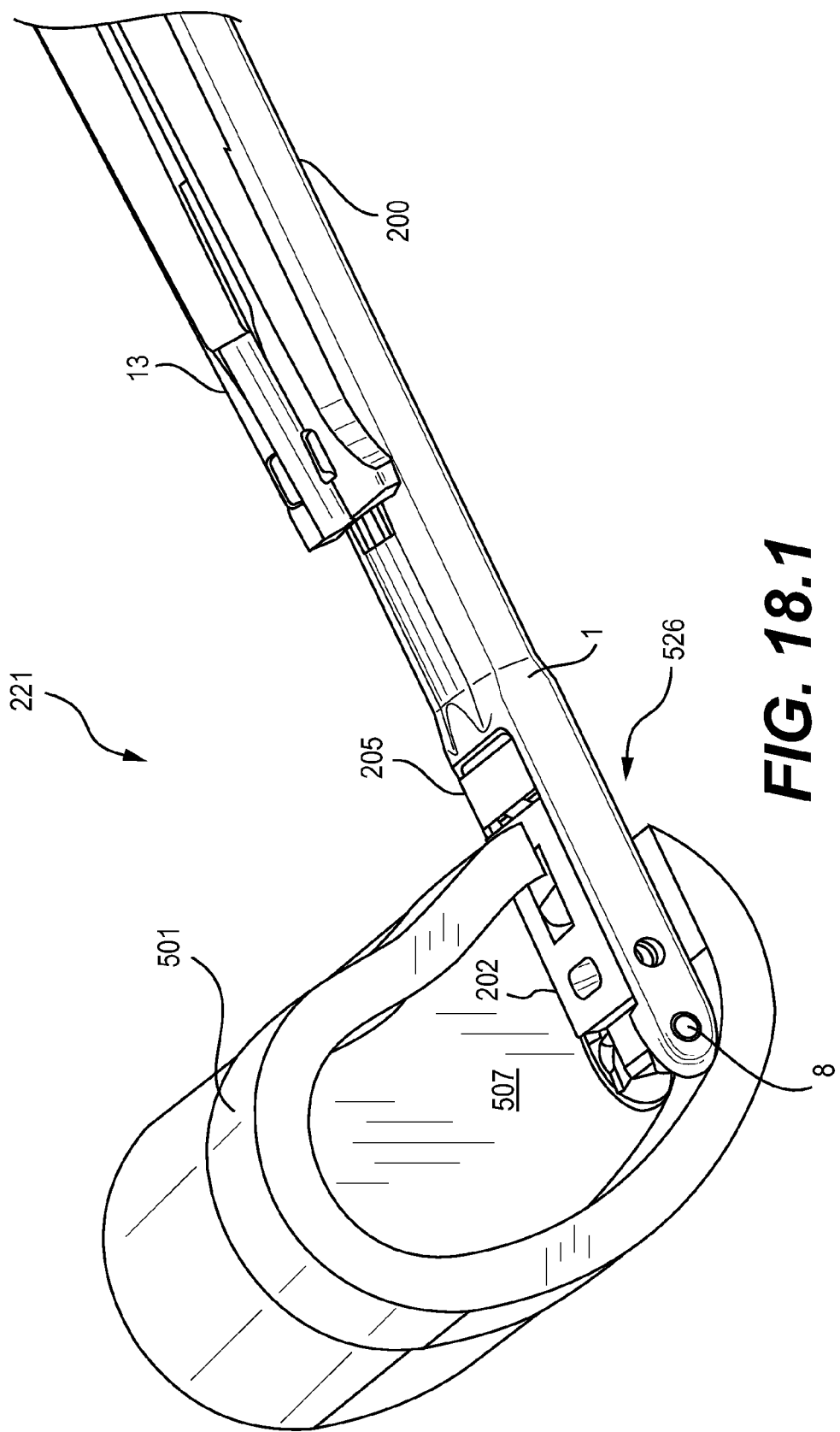
FIG. 18.1

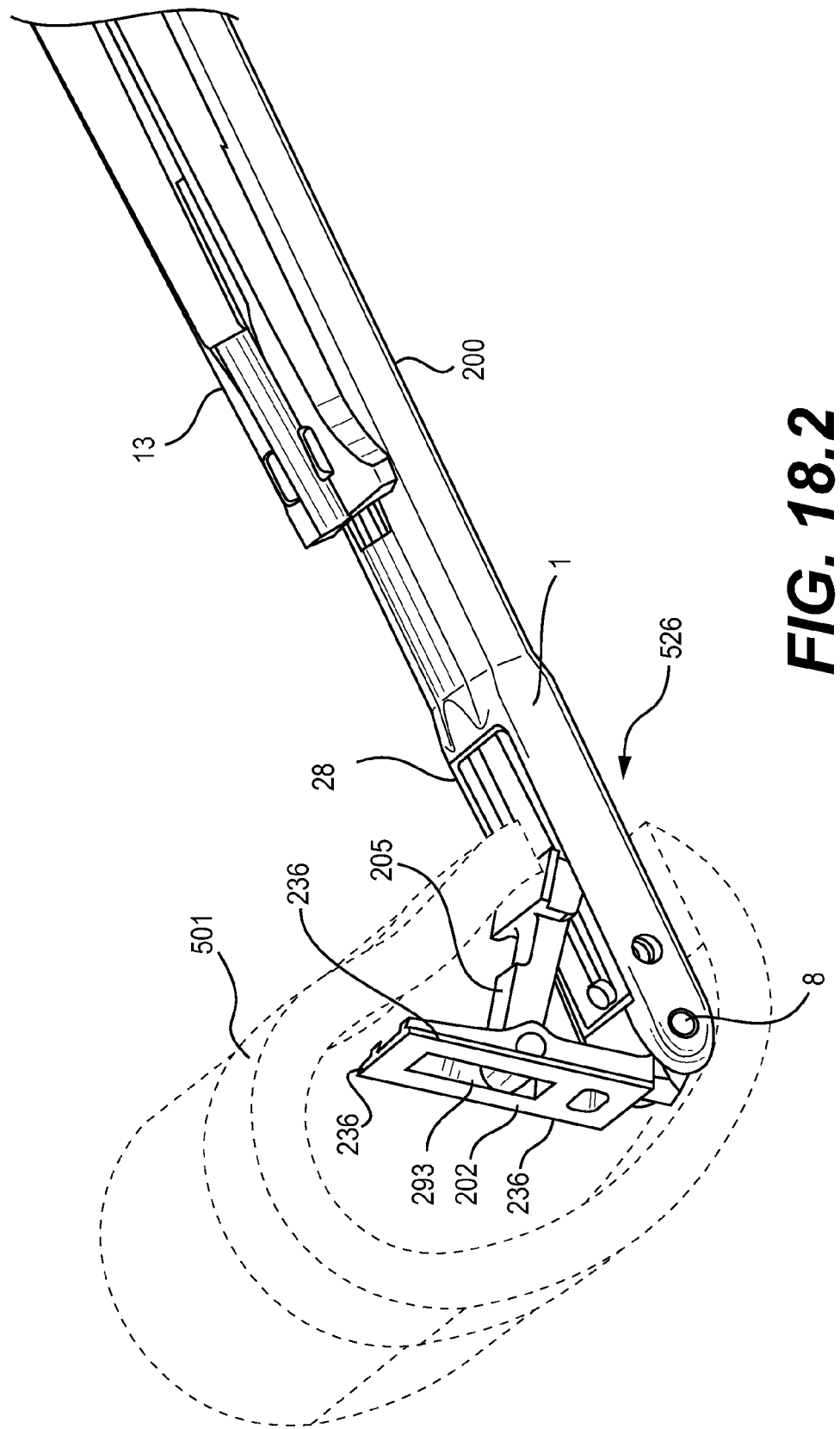
FIG. 18.2

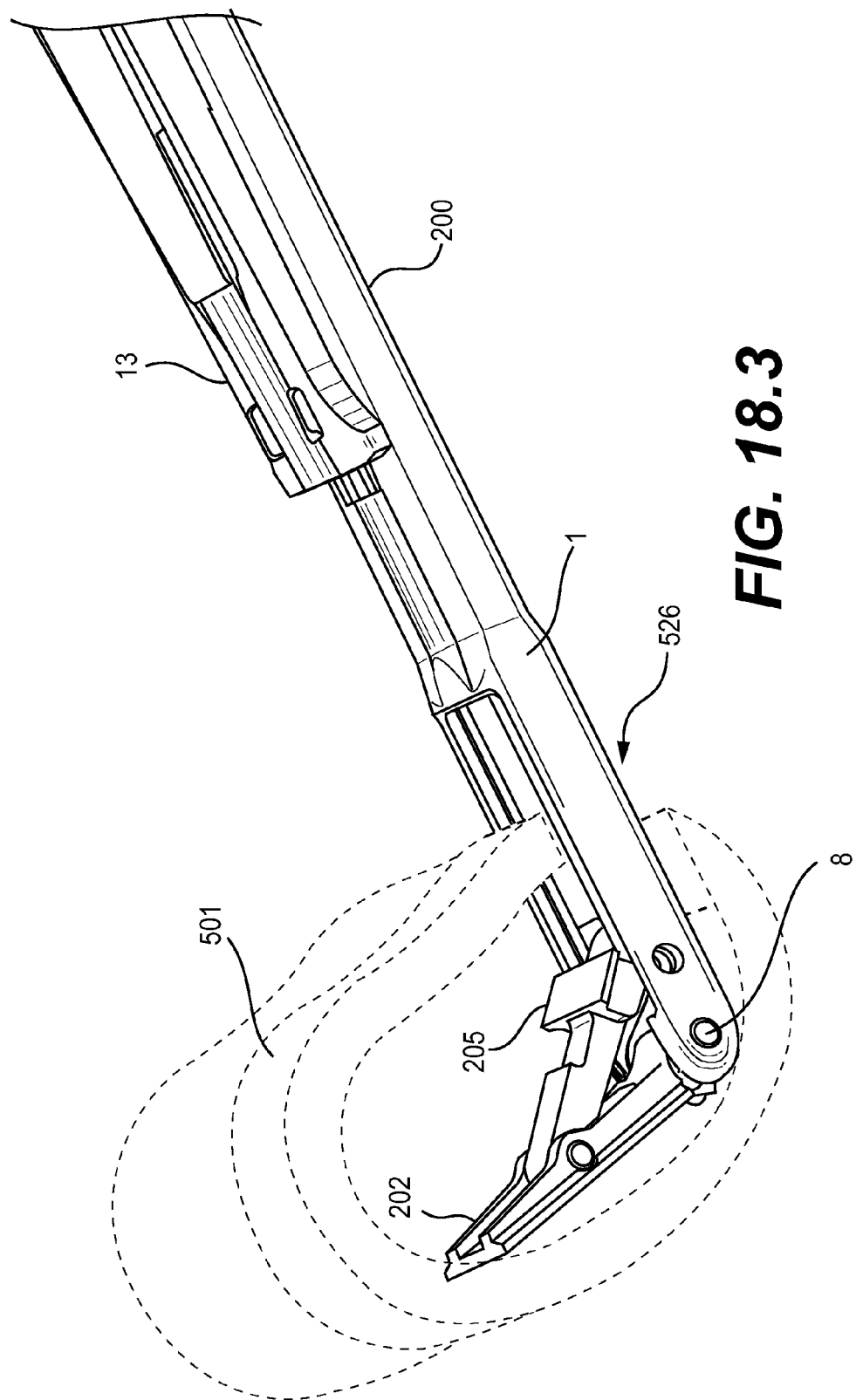
FIG. 18.3

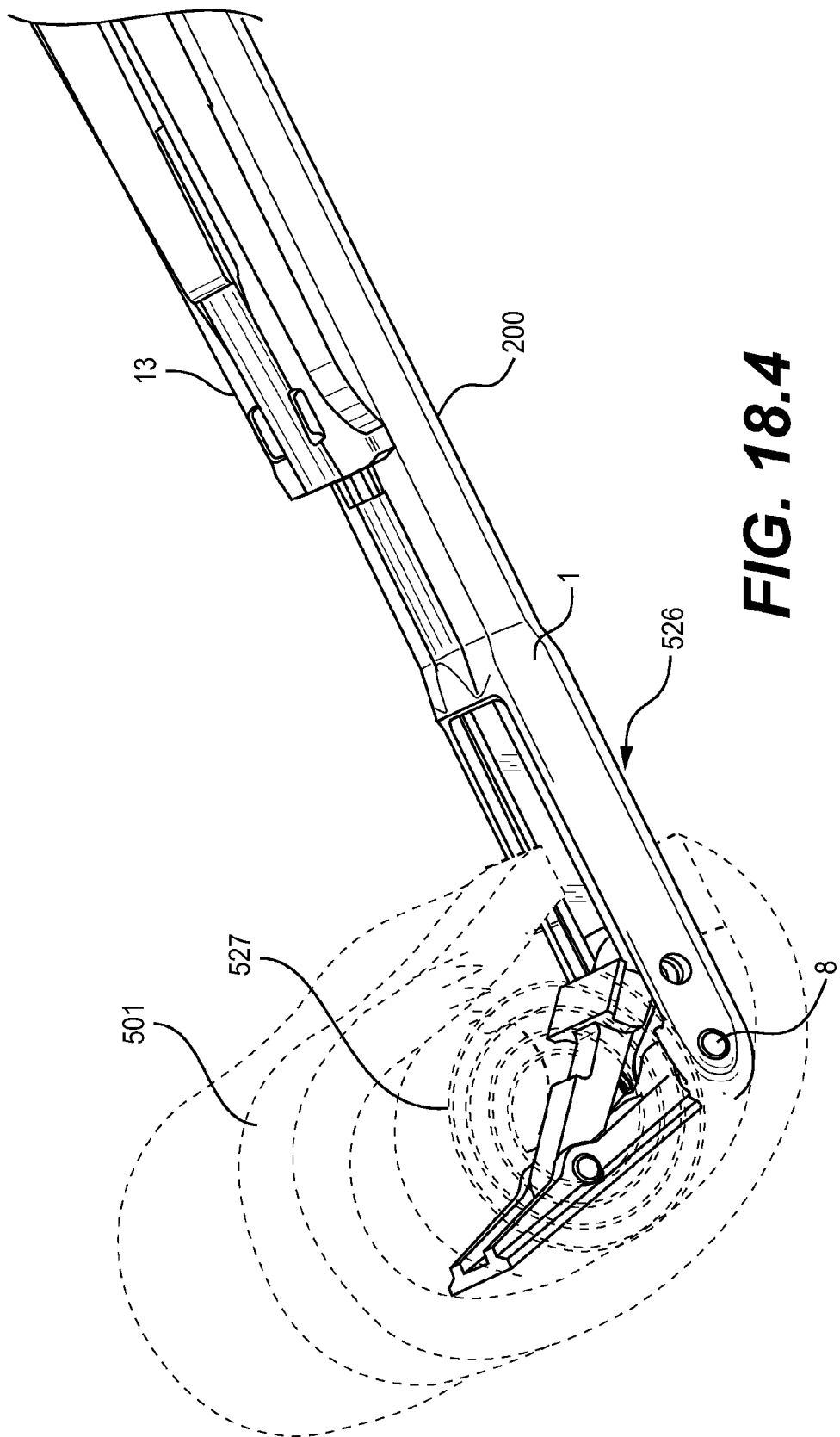

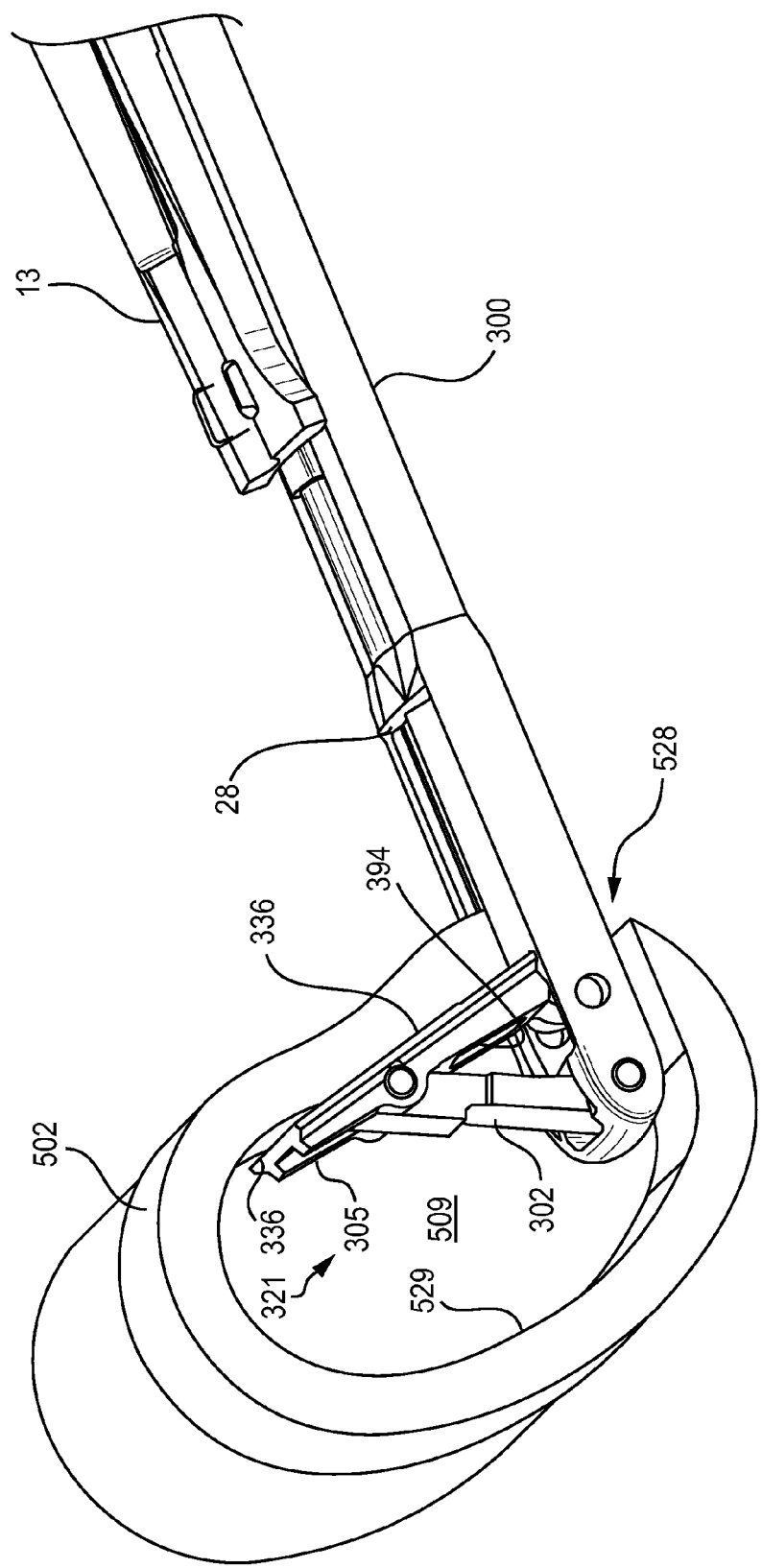
FIG. 19.1

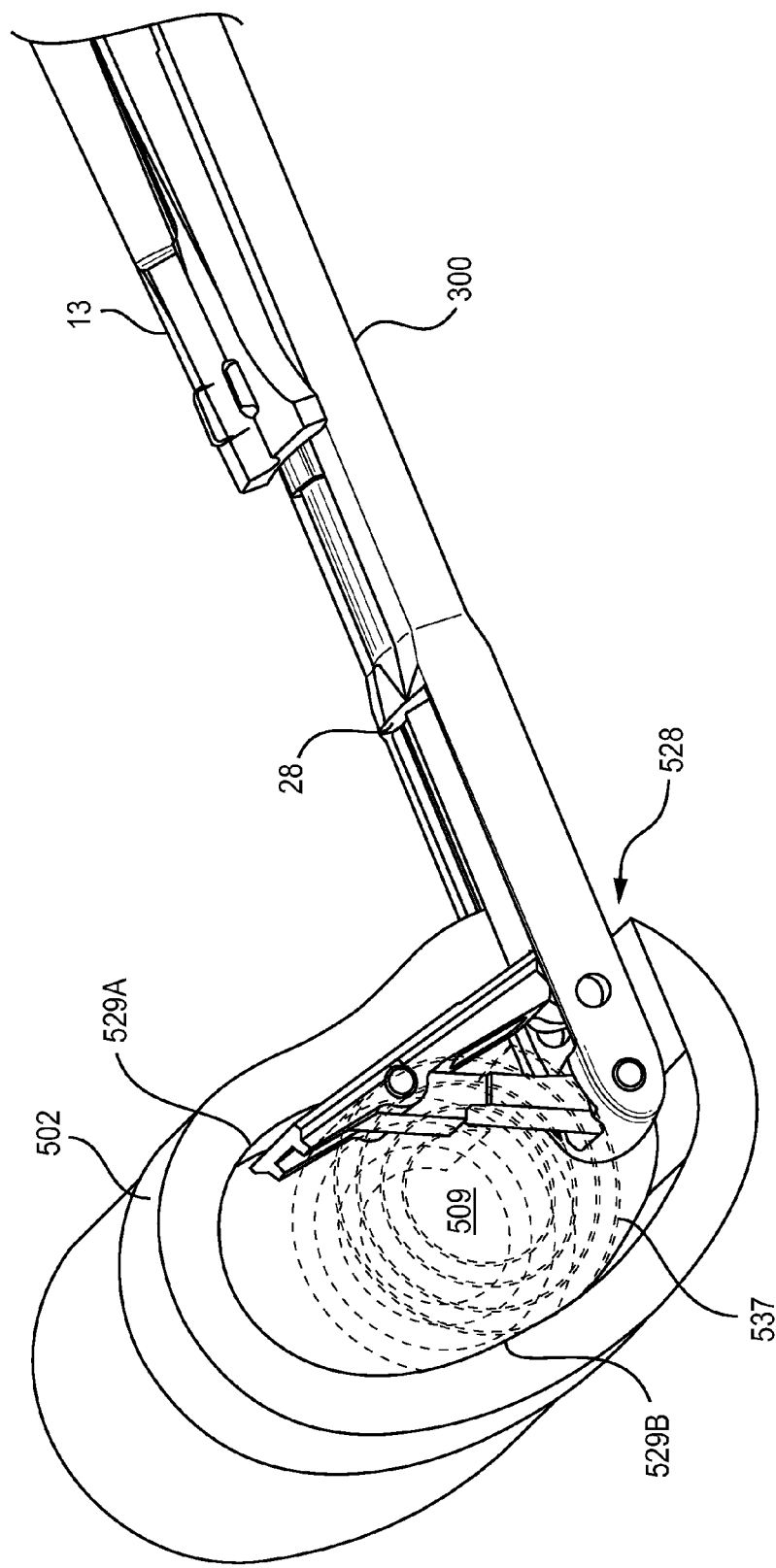
FIG. 19.2

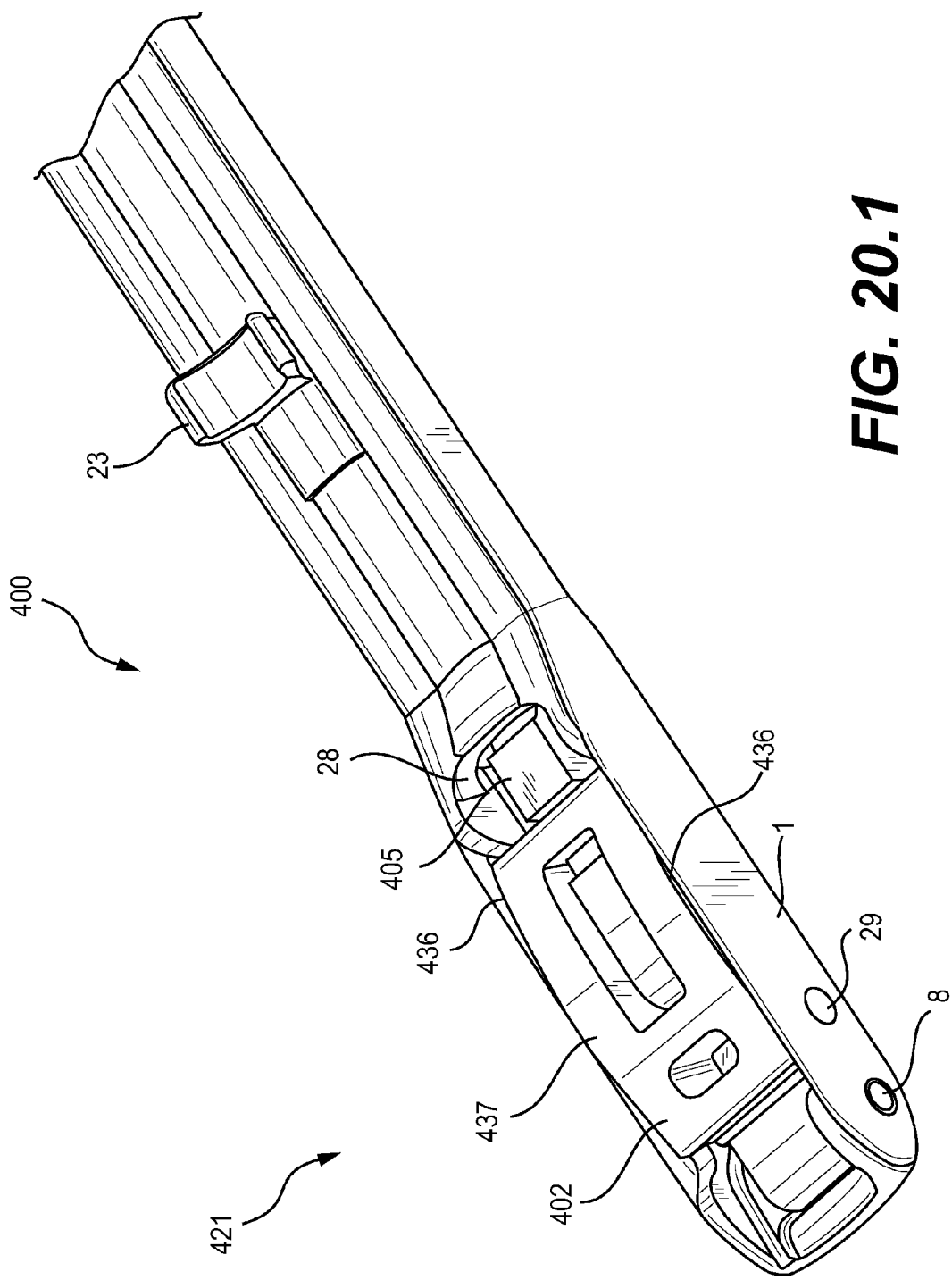
FIG. 20.1

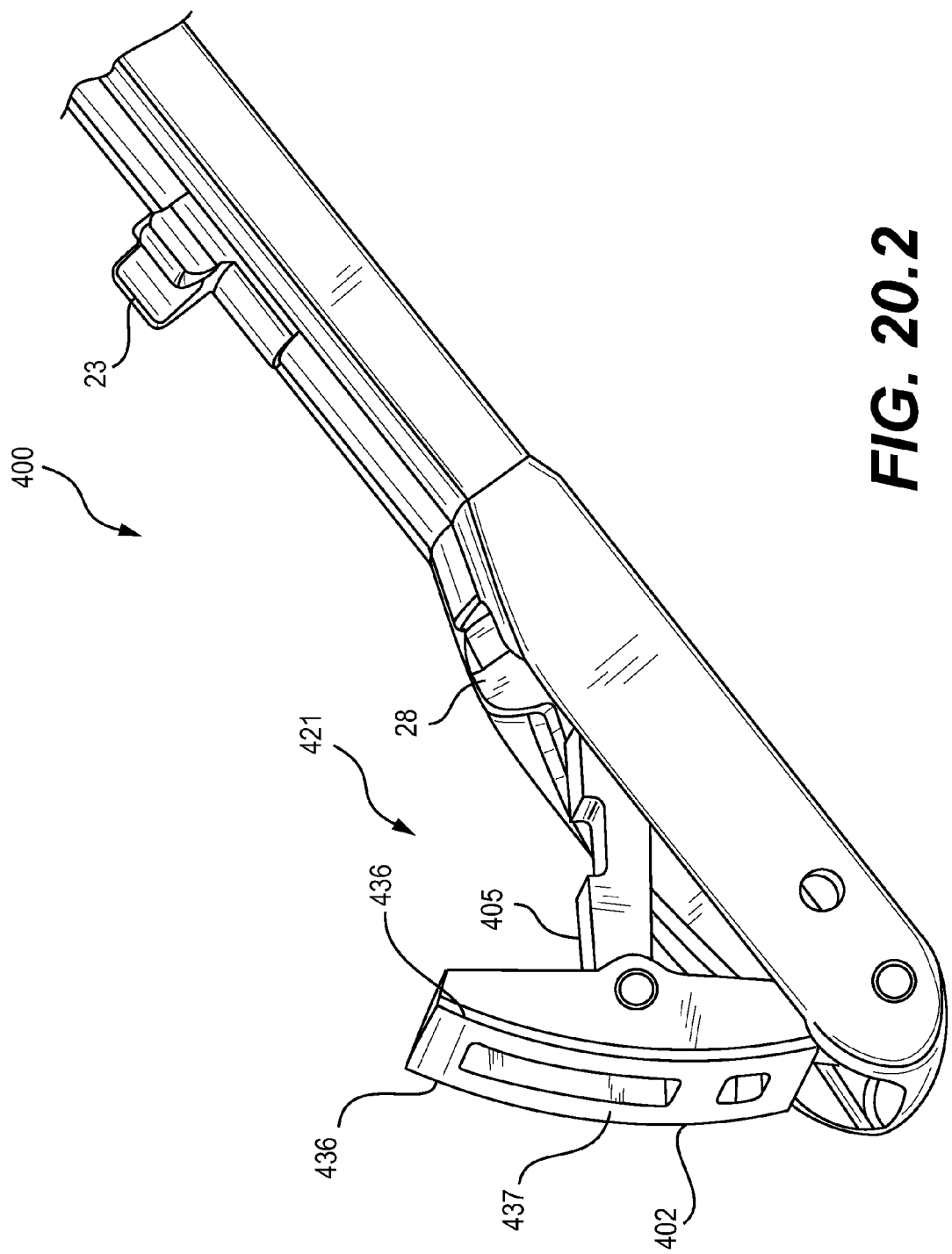
FIG. 20.2

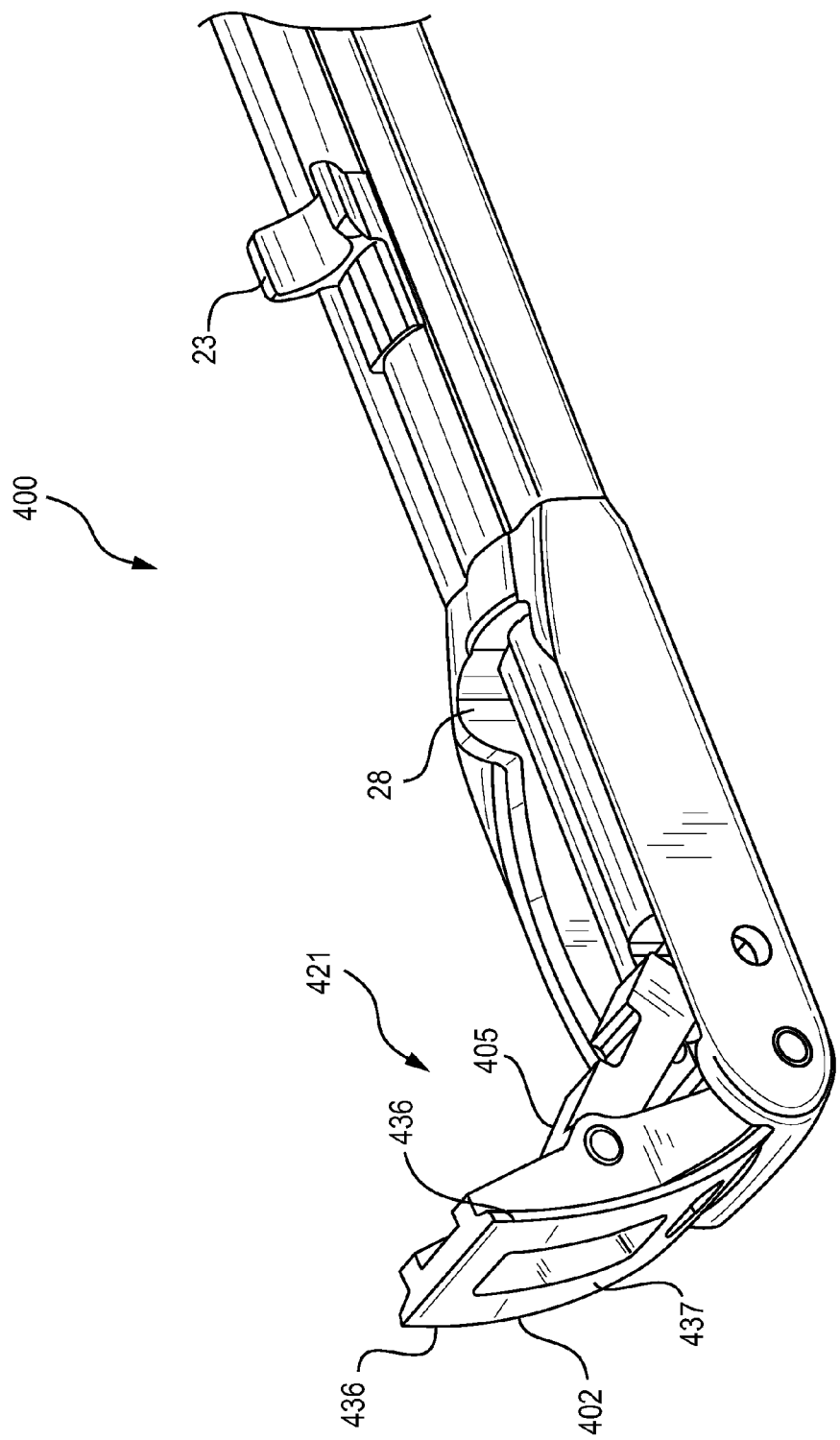
FIG. 20.3

DEVICES AND METHODS FOR PREPARATION OF VERTEBRAL MEMBERS

This application claims the benefit of U.S. Provisional Patent Application No. 61/919,994, filed Dec. 23, 2013, which is herein incorporated by reference in its entirety.

BACKGROUND

Field

The present embodiments relate to devices and methods for preparing surgical sites, and in particular, vertebral members, and more particularly, to devices and methods for preparing an intervertebral space between two adjacent vertebral bodies of two vertebrae of a spinal column, including, for example, sizing, surface preparation, and distraction.

Background

There remains a need for devices and methods for preparing a surgical site, and in particular, for preparing an intervertebral space for receiving an implant, such as a vertebral fusion implant.

SUMMARY

Embodiments provide devices and methods for preparing surgical sites, and in particular, vertebral members. Vertebral members may include, for example, any structures or corresponding spaces associated with a spine, including without limitation vertebrae, disc annuluses, disc nucleuses, cartilage, endplates, and ligaments.

In one aspect, a device for preparation of a surgical site may include a retractable tool and an actuator connected to the retractable tool. The retractable tool may include a distal member and a proximal member. A distal side of the distal member may be fixed in a longitudinal direction and pivotable at a point of rotation. A proximal side of the proximal member may be pivotably connected to the actuator. In a retracted position, the distal member may be pivotably connected to the proximal member longitudinally in between the point of rotation and the proximal side of the proximal member. Moving the actuator in a distal direction may push the proximal member and the distal member such that the proximal member pivots with respect to the actuator and the distal member, the distal member pivots with respect to the proximal member and the point of rotation, and the proximal member and the distal member move laterally outward with respect to the longitudinal direction.

In another aspect, the actuator may include an actuator rod and an actuator handle. A distal end of the actuator rod may be connected to the proximal end of the proximal member. A proximal end of the actuator rod may be connected to the actuator handle.

In another aspect, the actuator rod may be connected to the proximal member of the retractable tool by a threaded connection. Rotation of the actuator rod may adjust the distance between the actuator handle and the proximal member.

In another aspect, the device may further include a cannula. The actuator rod may be disposed within the cannula. The cannula may define an opening at a tip portion of the device. The proximal member and the distal member may be disposed within the opening when in the retracted position. The distal end of the distal member may be pivotably connected to the cannula at a distal end of the opening. The proximal member and the distal member may extend out of the opening when the actuator rod moves in the distal direction.

In another aspect, in the retracted position, an outer surface of the proximal member, an outer surface of the distal member, and an outer surface of the cannula around the opening may be generally flush with each other.

In another aspect, the device may further include a locking mechanism that prevents movement of the actuator rod in the longitudinal direction but allows rotational movement of the actuator rod.

In another aspect, the locking mechanism may include at least one of annular ribs and annular grooves on the actuator rod, and a button having at least one of annular ribs and annular grooves that engage and disengage the at least one of annular ribs and annular grooves of the actuator rod.

In another aspect, the device may further include a fixed handle on a proximal side of the cannula. Travel of the actuator handle in a distal direction may be limited by contacting the fixed handle.

In another aspect, at least one of the proximal member, the distal member, and the cannula may have surface structures for modifying a surface of a vertebral member.

In another aspect, the device may further include a depth gauge assembly.

In another aspect, the device may be used for sizing, surface preparation, or distraction.

In another aspect, a proximal end of the distal member may be pivotably connected to a distal end of the proximal member.

In another aspect, a distal end of the proximal member may be pivotably connected to an intermediate portion of the distal member. In the retracted position, an extension portion of the distal member may extend beyond the distal end of the proximal member toward the proximal end of the proximal member, and overlap the proximal member.

In another aspect, the proximal member may define a recessed portion for receiving the extension portion of the distal member so that an outer surface of the distal member and an outer surface of the proximal member are substantially flush when in the retracted position.

In another aspect, a proximal end of the distal member may be pivotably connected to an intermediate portion of the proximal member. In the retracted position, an extension portion of the proximal member may extend beyond the proximal end of the distal member toward the distal end of the distal member, and overlap the distal member.

In another aspect, the distal member may define a recessed portion for receiving the extension portion of the proximal member so that an outer surface of the proximal member and an outer surface of the distal member are substantially flush when in the retracted position.

In another aspect, at least one of the proximal member and the distal member may be shaped to match a shape of an implantation site.

Another aspect provides a device for preparing a surgical site. The device may extend from a proximal handle portion to a distal tip portion, and may define a longitudinal axis. The device may include a cannula, a cannula handle, an actuator rod, an actuator handle, a distal member, and a proximal member. The cannula may extend generally along the longitudinal axis and define an opening at a distal portion of the cannula. The cannula handle may be fixed to a proximal portion of the cannula. The actuator rod may be disposed within the cannula and moveable within the cannula in a longitudinal direction generally along the longitudinal axis. The actuator handle may be attached to a proximal portion of the actuator rod and may be disposed proximal to the cannula handle. A distal side of the distal member may be pivotably connected at a first point to a distal portion of the cannula. A proximal side of the proximal member may be pivotably connected to the actuator rod at a second point. In a retracted position, the distal member may be pivotably connected to the proximal member longitudinally in between the first point and the second point. In the retracted position, the distal member and the proximal member may be disposed within the cannula at the opening and may extend generally along the longitudinal direction. From the retracted position, moving the actuator rod in a distal direction relative to the cannula may push the proximal member and the distal member such that the proximal member pivots with respect to the actuator rod and the distal member, the distal member pivots with respect to the proximal member and the first point, and the proximal member and the distal member move laterally out of the opening.

In another aspect, the actuator rod may be connected to the proximal member by a longitudinally adjustable connection, and rotation of the actuator rod may adjust the distance between the actuator handle and the proximal member.

In another aspect, the device may include a locking mechanism that, in an extended position of the distal member and the proximal member, prevents movement of the actuator rod in the longitudinal direction but allows rotational movement of the actuator rod.

Another aspect provides a method for preparing a surgical site. The method includes inserting into the surgical site a device in a retracted position. The device may have a retractable tool and an actuator connected to the retractable tool. The retractable tool may include a distal member and a proximal member. A distal side of the distal member may be fixed in a longitudinal direction and pivotable at a point of rotation. A proximal side of the proximal member may be pivotably connected to the actuator. In the retracted position, the distal member may be pivotably connected to the proximal member longitudinally in between the point of rotation and the proximal side of the proximal member. In the retracted position, the distal member and the proximal member may extend generally along the longitudinal direction. The method may further include moving the actuator in a distal direction so that the actuator pushes the proximal member and the distal member such that the proximal member pivots with respect to the actuator and the distal member, the distal member pivots with respect to the proximal member and the point of rotation, and the proximal member and the distal member move laterally outward with respect to the longitudinal direction and across the surgical site.

In another aspect, the method further includes sizing the surgical site using the extended proximal member and the extended distal member.

In another aspect, the method further includes cutting the surgical site using the extended proximal member and the extended distal member.

In another aspect, the method further includes distracting the surgical site using the extended proximal member and the extended distal member.

In another aspect, the method further includes locking the actuator to prevent longitudinal movement of the actuator when the proximal member and the distal member are in a fully extended position, and moving the device such that the fully extended proximal member and the fully extended distal member move within the surgical site.

In another aspect, the method further includes moving the actuator in a proximal direction so that the actuator pulls the proximal member and the distal member such that the proximal member pivots with respect to the actuator and the distal member, the distal member pivots with respect to the proximal member and the point of rotation, and the proximal member and the distal member move laterally inward with respect to the longitudinal direction to the retracted position.

Other systems, methods, features, and advantages of the present embodiments will be, or will become, apparent to one with skill in the art upon examination of the following figures and detailed description. It is intended that all such additional systems, methods, features, and advantages be included within this description, be within the scope of the present embodiments, and be protected by the following claims.

BRIEF DESCRIPTION OF THE DRAWINGS

The present embodiments can be better understood with reference to the following drawings and description. The components in the figures are not necessarily to scale, emphasis instead being placed upon illustrating the principles of the present embodiments. Moreover, in the figures, like reference numerals designate corresponding parts throughout the different views.

FIG. 1.1 is a schematic diagram of a perspective view of an embodiment of a device for preparation of surgical sites, and in particular, vertebral members;

FIG. 1.2 is a schematic diagram of a partial plan view of the handle portion and tip portion of the device of FIG. 1.1;

FIG. 1.3 is a schematic diagram of an end view of the device of FIG. 1.1 looking in a longitudinal direction from the tip portion toward the handle portion;

FIG. 1.4 is a schematic diagram of a cross-sectional view of the device of FIG. 1.1 taken along section A-A of FIG. 1.3;

FIGS. 8.1-8.3 are schematic diagrams of full and partial cross-sectional views of the device of FIG. 1.1;

FIGS. 14.1-14.4 are schematic diagrams of an embodiment of a depth gauge assembly;

FIG. 15.1 is a schematic diagram of a perspective view of another embodiment of a retractable tool of a device for preparation of surgical sites, and in particular, vertebral members, shown in the retracted position;

FIG. 15.2 is a schematic diagram of a perspective view of the retractable tool of FIG. 15.1, shown at an intermediate position between the retracted position and the fully extended position, as an actuator handle attached to the retractable tool is rotated or moved in a distal direction;

FIG. 15.3 is a schematic diagram of a perspective view of the retractable tool of FIG. 15.1, shown in the fully extended position;

FIG. 16.1 is a schematic diagram of a perspective view of another embodiment of a retractable tool of a device for preparation of surgical sites, and in particular, vertebral members, shown in the retracted position;

FIG. 16.2 is a schematic diagram of a perspective view of the retractable tool of FIG. 16.1, shown at an intermediate position between the retracted position and the fully extended position, as an actuator handle attached to the retractable tool is rotated or moved in a distal direction;

FIG. 16.3 is a schematic diagram of a perspective view of the retractable tool of FIG. 16.1, shown in the fully extended position;

FIGS. 18.1-18.4 are schematic diagrams illustrating an embodiment of a method for preparation of surgical sites, and in particular, vertebral members, using the device of FIG. 15.1;

FIGS. 19.1-19.2 are schematic diagrams illustrating an embodiment of a method for preparation of surgical sites, and in particular, vertebral members, using the device of FIG. 16.1;

FIGS. 20.1-20.3 are schematic diagrams of perspective views of an alternative embodiment of a retractable tool of a device for preparation of surgical sites, and in particular, vertebral members, having specially shaped or contoured surfaces.

DETAILED DESCRIPTION

Figure 2:
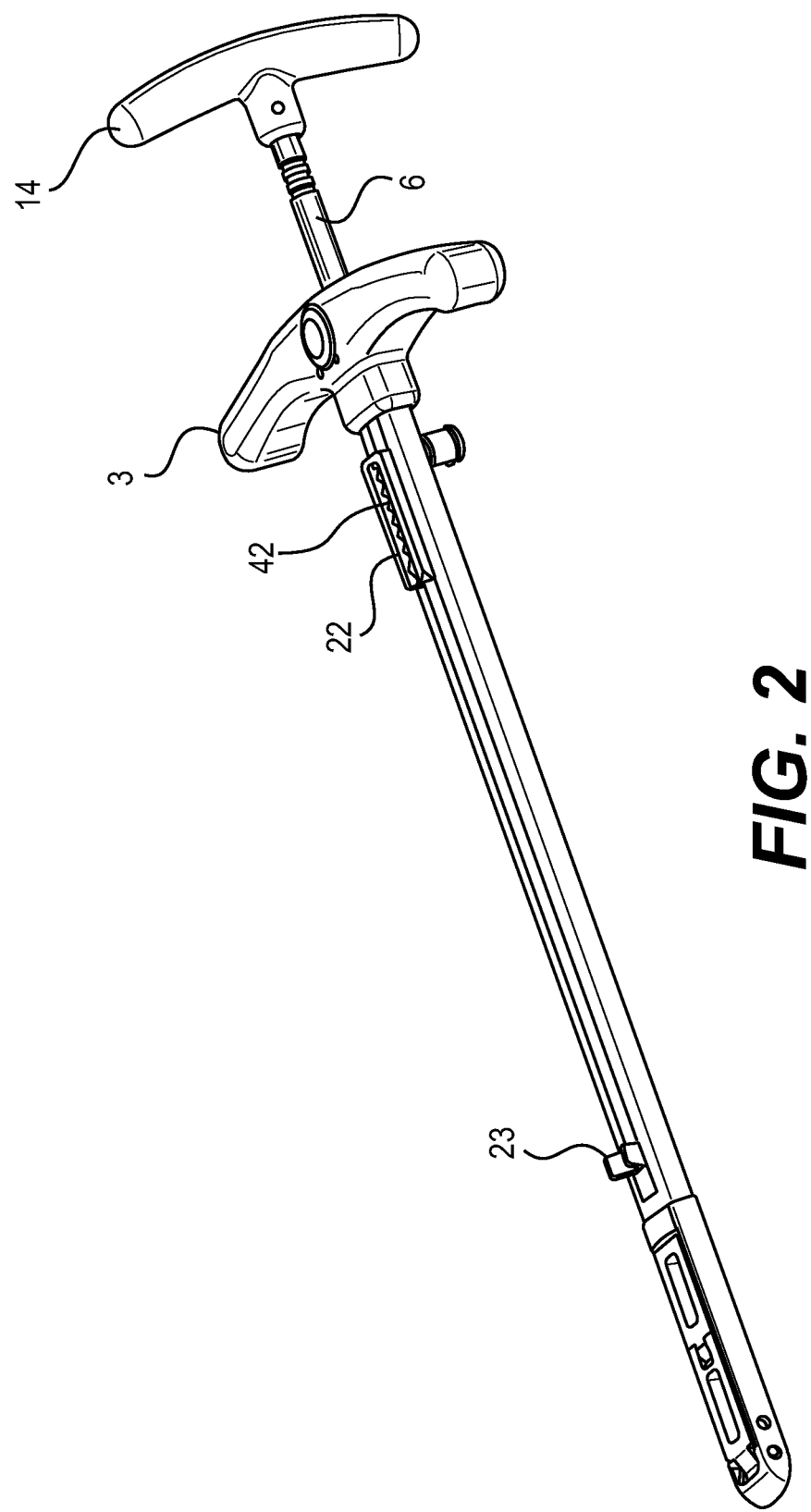
FIG. 2 is a schematic diagram illustrating the device of FIG. 1.1 in a retracted position, with the actuator handle pulled back and with the retractable A-frame members of the retractable tool retracted.

Embodiments provide devices and methods for preparing surgical sites, and in particular, for preparing vertebral members for receiving an implant.

Based on experience with implanting spinal fusion implants (e.g., spinal fusion implants made of coiled metal strips) in cadaver laboratory tests, the inventors found that disc nucleus preparation completed through a small incision opening in the annulus, i.e., small annulotomy (smaller than a coiled spinal fusion coil implant), may take a longer time than in an open procedure. A challenging aspect of the non-open procedures, such as minimally invasive spine surgeries or percutaneous procedures, is that a doctor may not be able to see how an instrument is affecting the area, e.g., when scraping. This area is preferably cleared of nucleus tissue and also cartilage on the vertebral endplates so that the vertebral endplate bone is exposed. The intervertebral space (also referred to herein as a void, void space, or disc space) is preferably geometrically precise in all directions to provide a good fit for a spinal fusion implant. If tissue or bone intrudes into the required discectomy void space, deployment of a spinal fusion implant may be inhibited. If excessive scraping occurs on the vertebral endplates, the softer cancellous bone may be exposed and compromise the structural bearing surface for the implant. Effective discectomy and endplate preparation helps ensure successful deployment and fusion of a spinal fusion implant, e.g., a spinal fusion coil. Examples of spinal fusion coils are disclosed in U.S. Pat. No. 7,922,767 to Sack et al., issued Apr. 12, 2011, and U.S. Pat. No. 8,197,548 to Sack et al., issued Jun. 12, 2012, both of which are herein incorporated by reference in their entirety. To view and prepare an intervertebral space, conventional methods have used large openings in the disc and have pounded, or otherwise forced, spinal fusion implants into place.

For consistency and convenience, directional adjectives are employed throughout this detailed description corresponding to the illustrated embodiments. The term "longitudinal," as used throughout this detailed description and in the claims, refers to a direction extending a length of a component. The term "longitudinal axis," as used throughout this detailed description and in the claims, refers to an axis oriented in a longitudinal direction. The term "lateral direction," as used throughout this detailed description and in the claims, refers to a side-to-side direction extending a width of a component. The term "lateral axis," as used throughout this detailed description and in the claims, refers to an axis oriented in a lateral direction. The term "horizontal," as used throughout this detailed description and in the claims, refers to any direction substantially parallel with the longitudinal direction, the lateral direction, and all directions in between. The term "vertical," as used throughout this detailed description and in the claims, refers to a direction generally perpendicular to both the lateral and longitudinal directions, along a vertical axis.

Embodiments provide an instrument that may rapidly check a discectomy void space, and may include further provisions for clearing a precisely sized and shaped void, free of imperfections such as divots and protrusions. In one embodiment, an instrument provides retractable members, such as A-frame members, that may move from a flat configuration for insertion through a small opening, to a raised configuration for checking the dimensions of an intervertebral space. An instrument may also include provisions for scraping vertebral bodies, such as rasp teeth, sharp edges, or other cutting structures on the retractable members and/or cannula tip.

FIGS. 1.1-1.4 illustrate an embodiment of a device 100 for preparation of surgical sites, and in particular, vertebral members. As shown, device 100 may include a tip portion 19 on a distal side of the device 100 and a handle portion 20 on a proximal side of the device 100. (As used herein, proximal and distal refer to positions relative to a position of a user of the device, such as a surgeon holding and using the device.) A cannula 1 may extend from the tip portion 19 to the handle portion 20. A fixed handle 3 may be affixed to the cannula 1 at the handle portion 20. The fixed handle 3 may be affixed to the cannula 1 using lock pins 12. A depth gauge assembly 13 may be affixed to an outer surface of the cannula 1, extending between the tip portion 19 and the handle portion 20. An actuator assembly may be disposed inside cannula 1, and may include an actuator handle 14 and an actuator rod 6, as shown in FIG. 2. The actuator assembly may be used to adjust the fully deployed height of a retractable tool 21 and to deploy and retract tool 21. The actuator rod 6 may be connected to the actuator handle 14 using a locking pin 11. As shown, the actuator handle 14 and fixed handle 3 may be T-shaped. A cannula, such as cannula 1, may have a generally constant cross-sectional size and shape from the tip portion to the handle portion, or may vary in cross-sectional size and shape, for example, depending on the particular surgical site for which a device is intended.

Tool 21 may include a slide connector 4 and A-frame members, including a distal member 2 and a proximal member 5. A proximal side of slide connector 4 may be connected to a distal side of the actuator rod 6, while a distal side of the slide connector 4 may be pivotably connected to a proximal side of the A-frame member 5 by a pivot pin 9A. A distal side of the A-frame member 5 may be pivotably connected to a proximal side of the A-frame member 2 by a pivot pin 9B. A distal side of the A-frame member 2 may be connected to the cannula 1 by a pivot pin 8. The pivotable connections associated with the tool 21 may allow the tool 21 to extend from, and retract into, an opening in the cannula 1 at the tip portion 19 of the device 100, as the slide connector 4 is moved distally and proximally by the actuator rod 6 of the actuator assembly.

A surgical site preparation device may include provisions for locking the position of a tool. As shown in FIGS. 1.1-1.4, for example, device 100 may include a lock mechanism, including a spring 10 and button 7 having locking structures that cooperate with locking structures on the actuator rod 6. The locking structures may be, for example, ribs and/or grooves that engage each other. The spring 10 and button 7 may be biased to engage the locking structures when the button 7 is in an extended, unpressed position, and to release the locking structures when the button 7 is pressed. As shown, the locking mechanism of device 100 may be disposed inside the fixed handle 3.

A surgical site preparation device may include provisions for adjusting the configuration of the device before use. As shown best in FIGS. 1.4, 8.1, 8.2, and 12, slide connector 4 may be adjustably connected to the actuator rod 6, for example, by a threaded connection that allows lengthwise adjustments along the longitudinal direction of the device 100. With this adjustable connection, the actuator handle 14 may be rotated to adjust and preset the fully deployed height of the pivoting A-frame members 2 and 5 of tool 21. As shown in the cross-sectional views of FIGS. 8.1 and 8.2, the actuator handle 14 may be rotated to advance or retract the threads of the distal end of the actuator rod 6 into or out of the threads of the slide connector 4, thereby adjusting the distance between the actuator handle 14 and the proximal A-frame member 5. In the depicted embodiment, the actuator rod 6 has a male threaded end that is received by a female threaded end of the slide connector 4, though the reverse threaded connection would suffice as well. In addition, other adjustable connections could be used. In the illustrated embodiment, by rotating the actuator handle 14, a user may preset the fully deployed height of the tool 21, for example, to size or expand an intervertebral space. This may be done while the device 100 is nested in a graduated feature of a sterilization tray in order to achieve the desired extension to match the implant.

To allow for the configuration adjustments, a lock mechanism of a surgical site preparation device may include provisions that permit rotation but limit or prevent axial movement. As shown in FIGS. 8.3 and 11, for example, lock button 7 may be spring loaded (by spring 10) outwardly to engage radial ribs and grooves 26 of button 7 with radial ribs and grooves 27 of actuator rod 6. An example of that type of engagement is shown at location 24 in FIGS. 8.3. The ribs and grooves may therefore permit rotational movement but not axial movement. As represented by the arrow 25 in FIG. 8.3, pressing the button 7 disengages the ribs and grooves.

Figure 3:
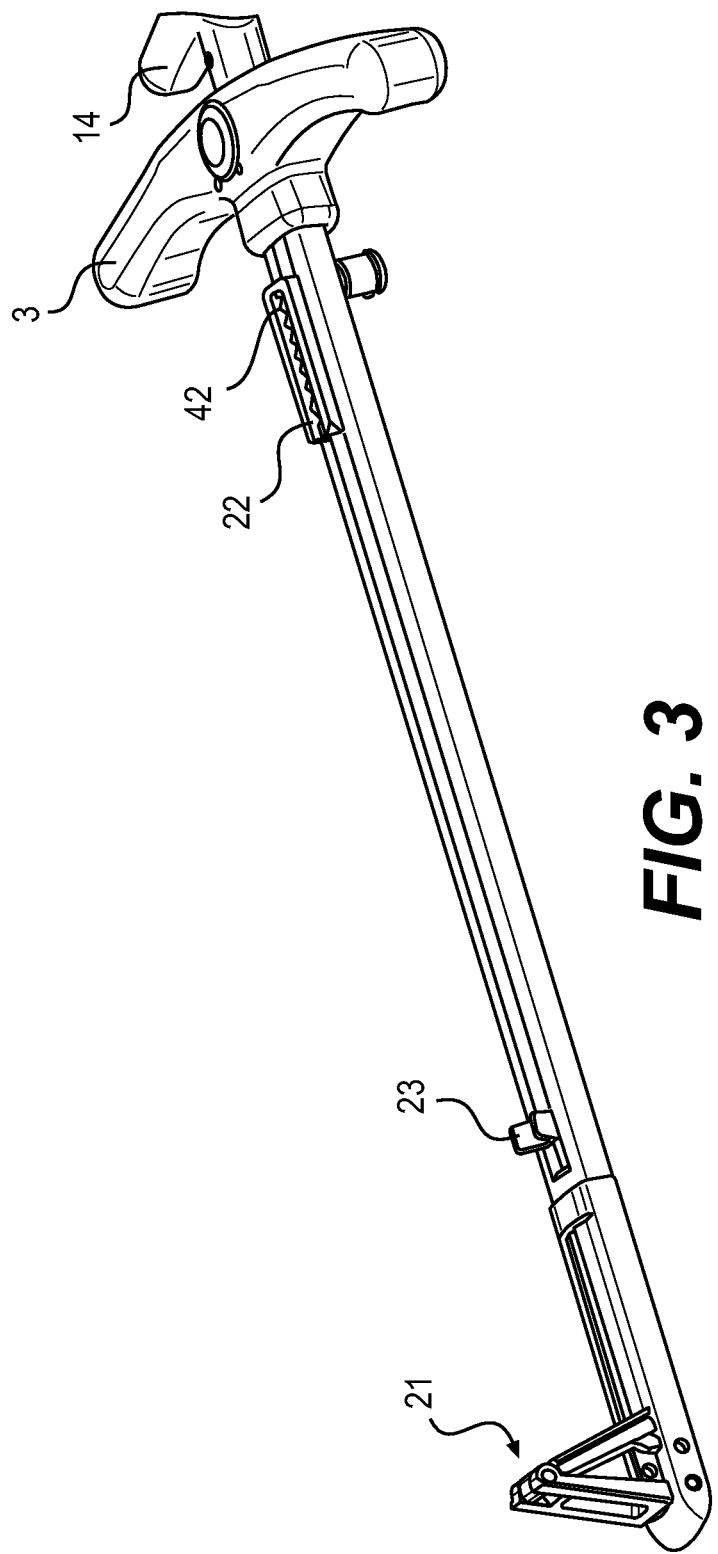
FIG. 3 is a schematic diagram illustrating the device of FIG. 1.1 in a deployed position, with the actuator handle pushed in and with the retractable members of the retractable tool fully extended.

After a configuration adjustment is made, the lock release button 7 may be depressed to allow the actuator handle 14 to be pulled back to collapse the A-frame members 2 and 5 of tool 21 for convenient insertion into a disc opening, as shown in FIG. 2, for example. The tip portion 19 of device 100 may be inserted to the correct depth into the disc space through an annulotomy and rotated 90 degrees. Then, the actuator handle 14 may be pushed inward until the actuator handle 14 clicks and locks into place, when one or more annular ribs and/or grooves of a spring loaded button 7 engage corresponding annular ribs and/or grooves of actuator rod 6. This action extends the A-frame members 2 and 5 to the preset fully deployed height, as shown in FIG. 3, for example. A user may then repeatedly push forward and pull back on the entire device (for example, holding the handle portion 20 of the device 100) to verify the size of a discectomy void space, or to cut bone or tissue.

Figure 11:
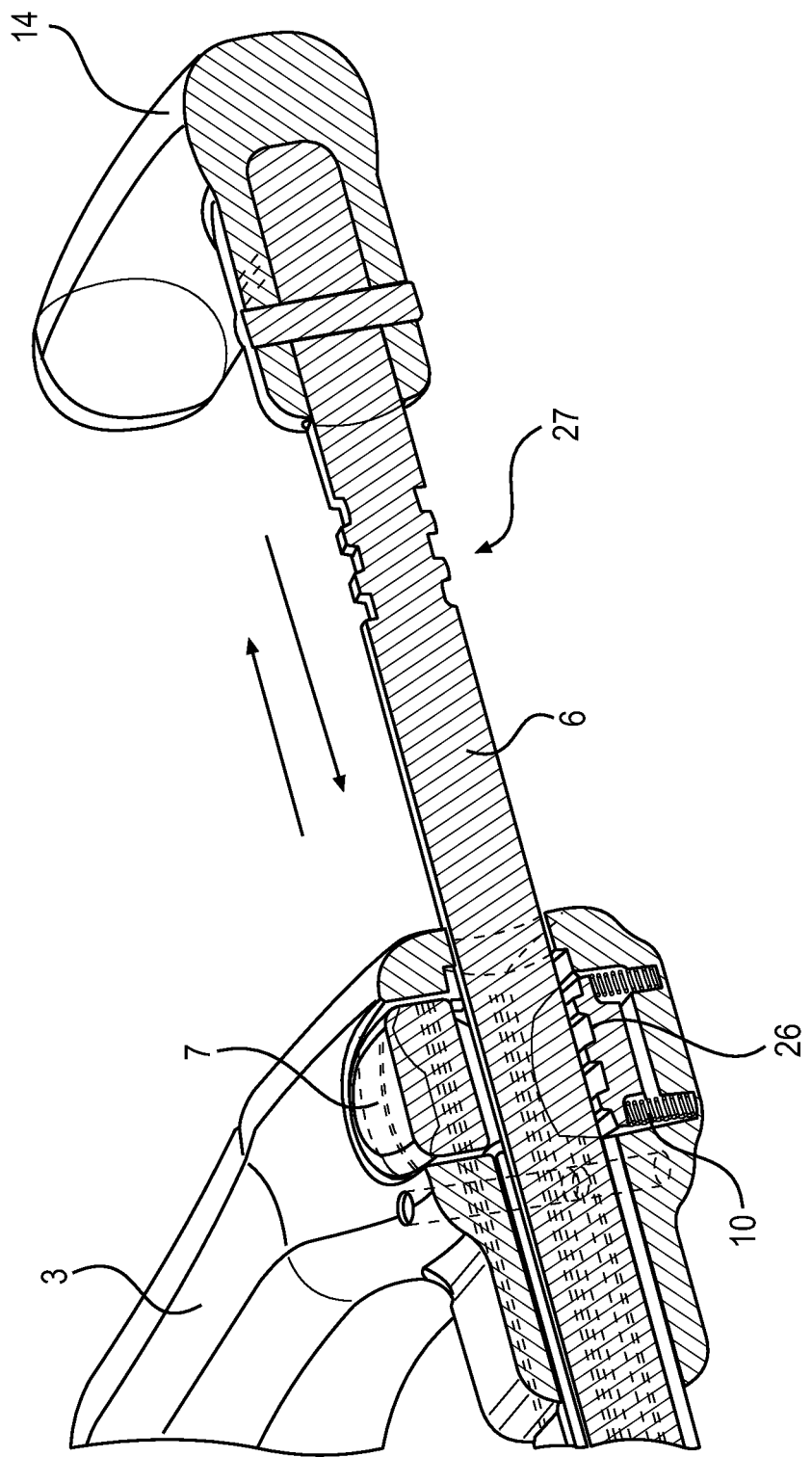
FIG. 11 is a schematic diagram of a cross-sectional view of the handle portion of the device of FIG. 1.1.

FIG. 11 illustrates an enlarged perspective view of an exemplary operation of a locking mechanism and actuator rod according to an embodiment. As shown, when lock button 7 is pressed against the force of the spring 10, the radial ribs and grooves 26 may disengage from the radial ribs and grooves 27 on the actuator rod 6. This disengagement allows the actuator rod 6 and the connected actuator handle 14, along with the slide connector 4 (not shown in FIG. 11), to freely move in an axial direction within travel limits. The outward limit may be determined by the full retraction of the A-frame members 2 and 5 into the opening 28 of the cannula 1. Inward travel may be limited by a distal side of the actuator handle 14 contacting a proximal side of the fixed handle 3. This travel distance may be determined by the number of turns applied to the actuator handle 14.

Figure 4:
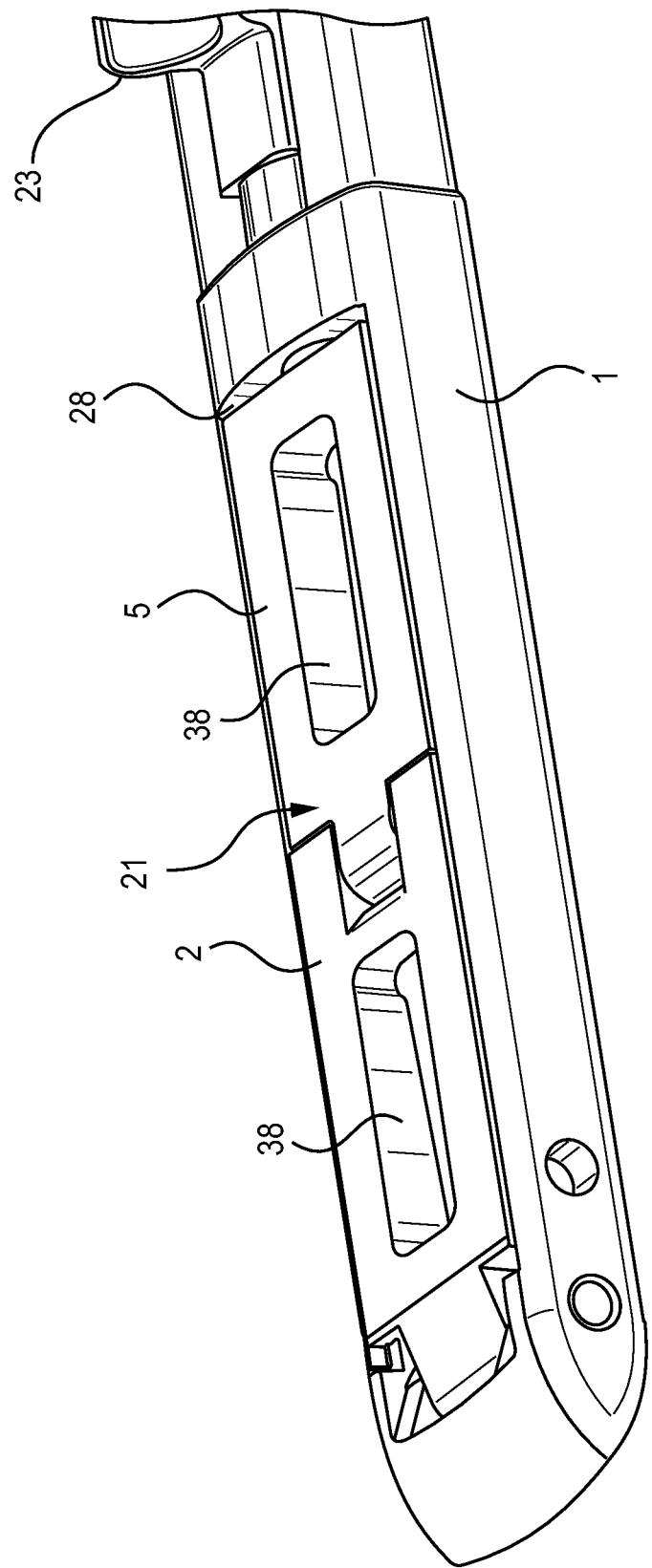
FIG. 4 is a schematic diagram of an enlarged view of the tip portion of the device of FIG. 1.1, with the retractable members fully retracted.
Figure 5:
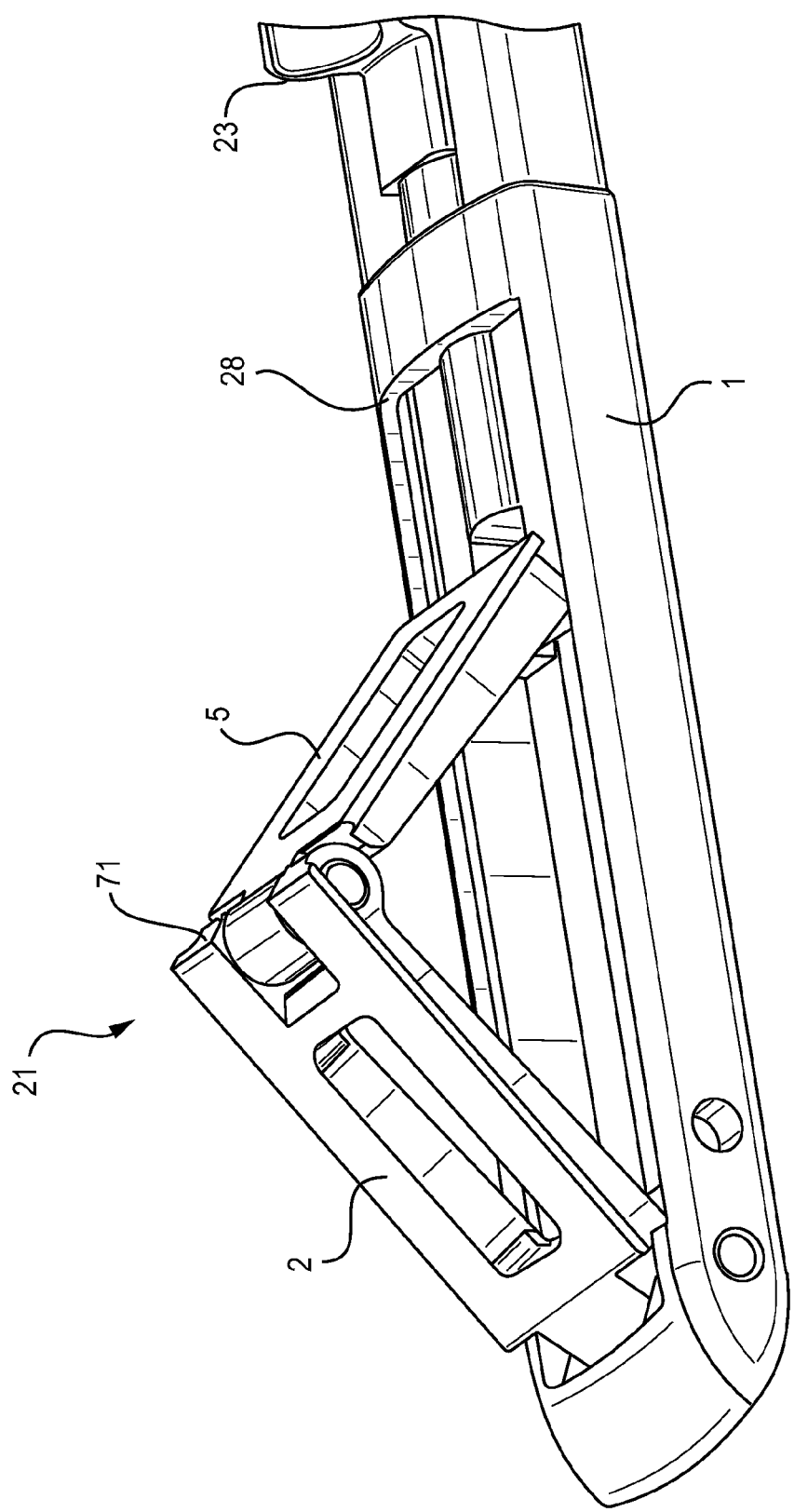
FIG. 5 is a schematic diagram of an enlarged view of the tip portion of the device of FIG. 1.1, with the retractable members beginning to extend as the actuator handle is rotated or moved in a distal direction.
Figure 6:
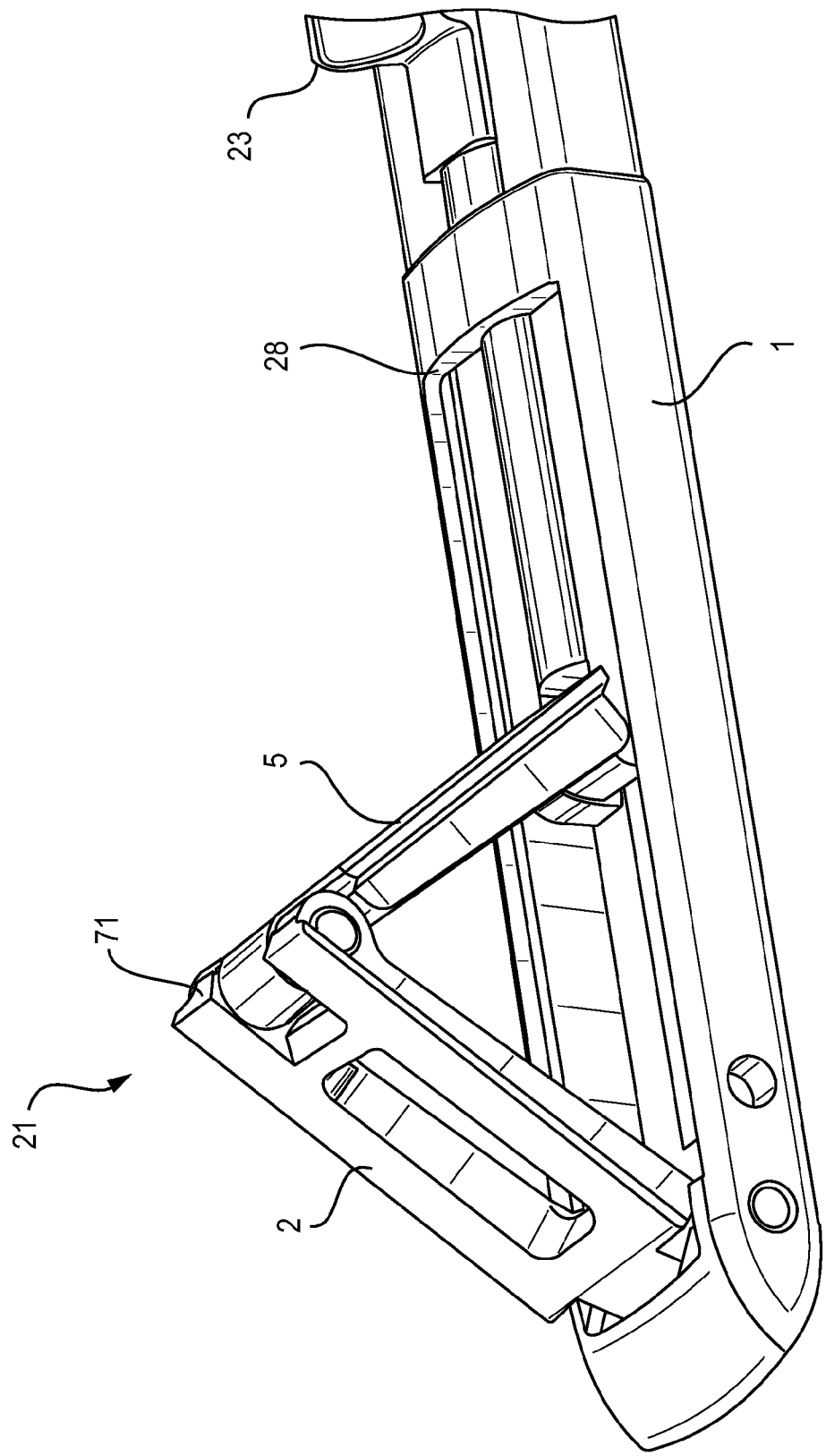
FIG. 6 is a schematic diagram of an enlarged view of the tip portion of the device of FIG. 1.1, with the retractable members continuing to extend in comparison to FIG. 5, as the actuator handle is further rotated or moved in a distal direction.
Figure 7:
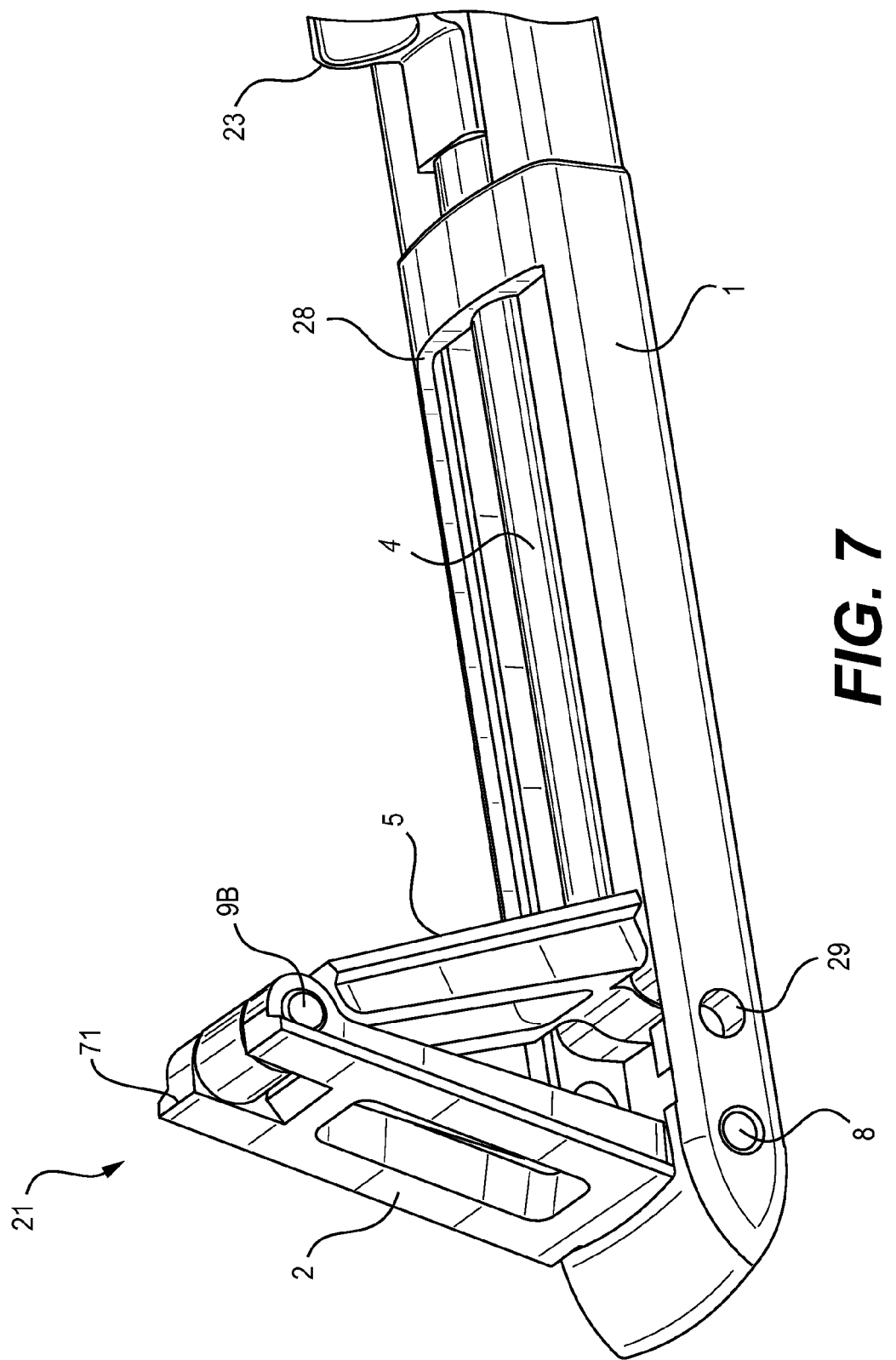
FIG. 7 is a schematic diagram of an enlarged view of the tip portion of the device of FIG. 1.1, with the retractable members fully extended.

FIGS. 4-7, 10, and 12 illustrate further details of the structure and operation of a retractable tool of a surgical site preparation device, according to embodiments. FIG. 4 illustrates tool 21 in a fully retracted position, with A-frame members 2 and 5 stowed in the opening 28 of cannula 1. FIG. 5 illustrates tool 21 in an intermediate position as the A-frame members 2 and 5 are extending out of the opening 28 of the cannula 1, as a result of either the rotation of the actuator handle 14 during a presetting period of adjustment or the axial movement of the actuator handle 14 in the distal direction during use. FIG. 6 illustrates tool 21 in a further intermediate position continuing toward its fully deployed position. FIG. 7 illustrates tool 21 in its fully deployed position, with A-frame members 2 and 5 at the fully extended height to which they were preset. FIG. 7 also shows a blank hole 29 in the cannula 1, which may be used to insert pivot pin 9A into the A-frame member 5 and slide connector 4 during assembly of the device 100.

Figure 9:
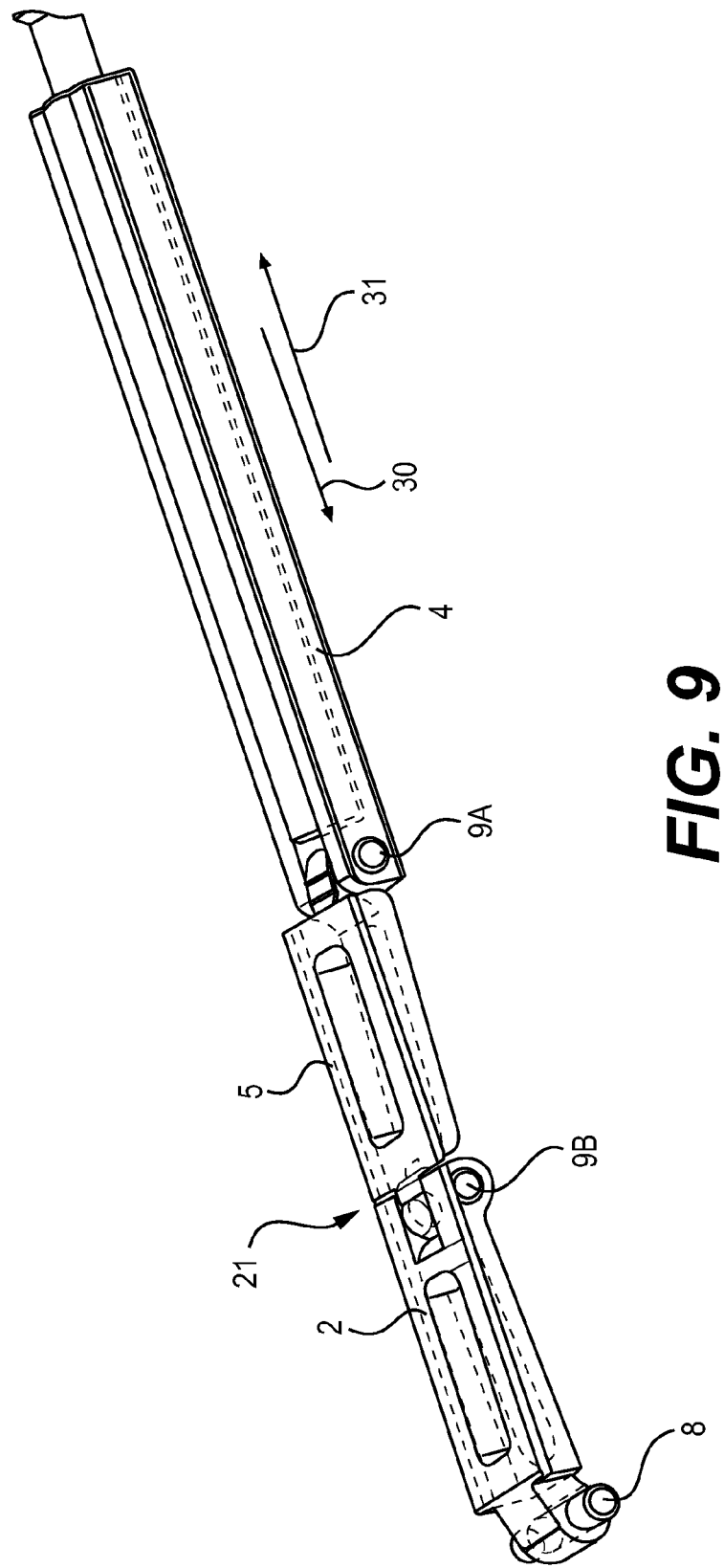
FIG. 9 is a schematic diagram of a perspective view of internal components of the device of FIG. 1.1.
Figure 10:
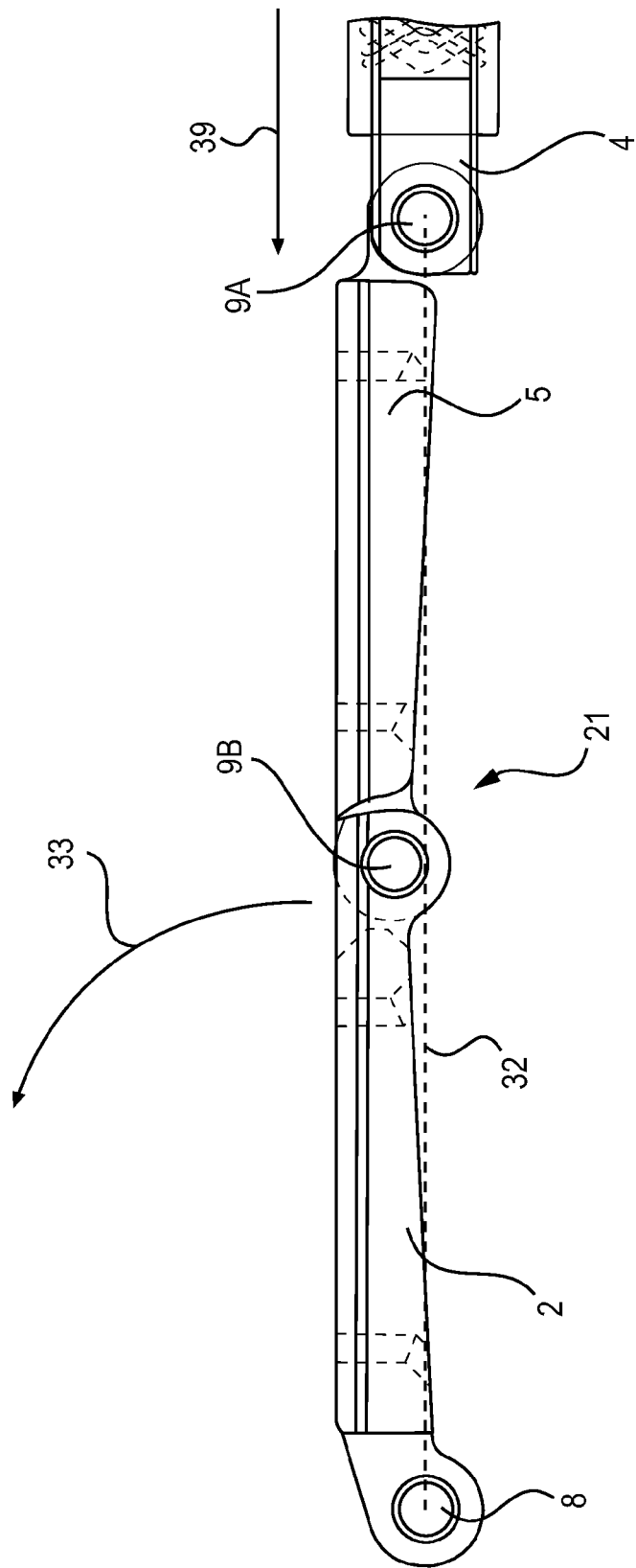
FIG. 10 is a schematic diagram of a side view of internal components of the device of FIG. 1.1.

For clarity purposes, FIGS. 9 and 10 illustrate the tool 21 and slide connector 4, without other portions of device 100, according to an embodiment. As shown, the pivotable connections between the tool 21, slide connector 4, and cannula 1 (not shown) allow the A-frame members 2 and 5 to pivot with respect to the slide connector 4, the cannula 1, and each other, to raise and lower for deployment and retraction, respectively. As represented by arrow 30 in FIG. 9, deployment may be accomplished by moving slide connector 4 in a distal direction to raise A-frame members 2 and 5. Subsequently, as represented by arrow 31 in FIG. 9, retraction may be accomplished by moving slide connector 4 back in a proximal direction to lower A-frame members 2 and 5.

As shown in FIG. 10, in an embodiment, pivot pin 9B may be configured to remain above a thrust center line 32 between pivot pin 8, which is fixed to the cannula 1, and pivot pin 9A, which moves as slide connector 4 moves (as represented by arrow 39). This offset position of pivot pin 9B above thrust center line 32 may ensure that the A-frame members 2 and 5 extend (as represented by arrow 33) and fully retract when actuated by the slide connector 4.

Figure 12:
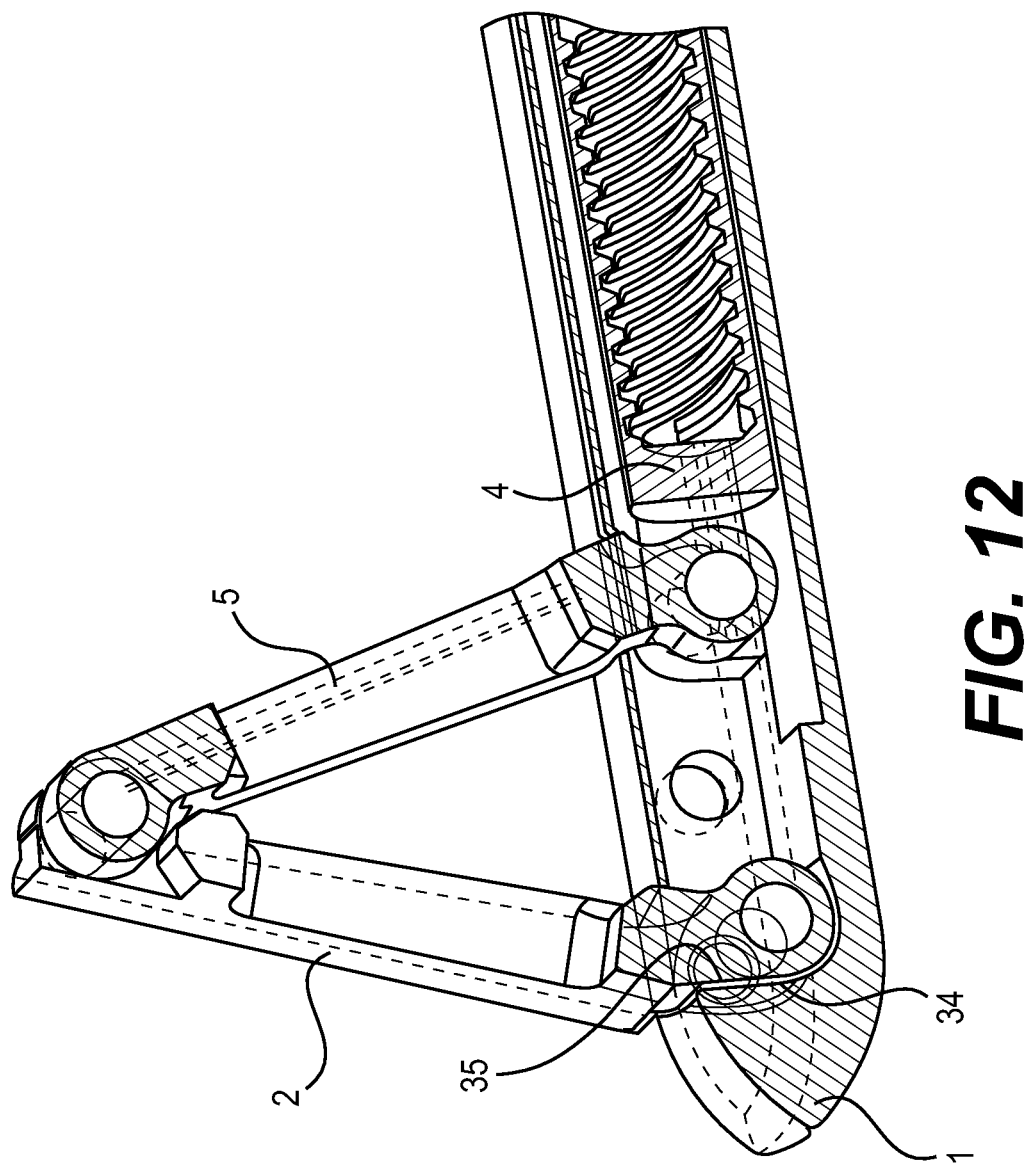
FIG. 12 is a schematic diagram of a cross-sectional view of the tip portion of the device of FIG. 1.1.

Embodiments may include provisions for securely limiting the travel of tool 21 when reaching the fully deployed position. As an example, the cross-sectional perspective view of FIG. 12 illustrates the travel of tool 21 limited by surface contact between an internal flat surface 34 of the cannula 1 and a corresponding flat surface 35 of the A-frame member 2. In adjusting the full deployment height of the tool 21 (as the actuator rod 6 and slide connector 4 rotate with respect to each other), a user may feel the contact between surfaces 34 and 35 as the actuator handle 14 is rotated while the ribs and grooves 27 of the actuator rod 6 are engaged with the ribs and grooves 26 of the button 7 (see, e.g., FIG. 11). This feel of contacting surfaces 34 and 35 may signal to the user that the tool 21 has reached its upper limit of travel and deployment height adjustment.

Embodiments may include provisions for limiting the insertion depth of the tip portion of the device 100. For example, as shown in FIGS. 1.4 and 14.1-14.4 an adjustable depth gauge assembly 13 may limit the instrument insertion depth into an annulotomy and may be aligned with numerical graduations that correspond to graduations on a corresponding deployment instrument used to deploy a spinal implant. This may allow quick and accurate depth control of the deployment instrument in reference to the newly cleared void so that a spinal implant is properly deployed, e.g., allowing a spinal fusion coil to automatically deploy in the correct location.

As shown in FIGS. 1.4, 2, 3, and 14.1-14.4, an embodiment of a depth gauge assembly 13 may include a depth gauge 15, a depth gauge lock 16, a fastener 17, a spring 18, and a mounting plate 22 and support 23 attached to the cannula 1. For purposes of illustration, FIGS. 2 and 3 depict the mounting plate 22 and support 23, without the remaining components of the depth gauge assembly 13. As shown in FIGS. 2 and 3, mounting plate 22 may include incremental ridges and openings 42 with which the depth gauge lock 16 may engage. For example, a U-shaped configuration of depth gauge lock 16, as shown in FIG. 14.4, may engage the complementary shape of the ridges and openings 42 of the mounting plate 22. The spring-mounted fastener 17 allows the depth gauge lock 16 to engage and disengage the mounting plate 22, to allow the depth gauge 15 to slide longitudinally along the mounting plate 22 and support 23 to a desired position at which point the depth gauge lock 16 may lock the depth gauge 15.

Some embodiments may include provisions for preparing surfaces of a surgical site, such as preparing surfaces of vertebral members for implantation. In embodiments, device 100 may have sharpened edges or file teeth on the A-frame members 2 and 5 and file teeth on the narrow edges of the tip portion of the cannula 1. Those provisions may allow a device 100 to be used as a rasp or scraper instrument to facilitate the cleanout of a disc space, and may facilitate the creation of a clear trapezoidal void space with a precise gap having parallel surfaces between vertebral endplates.

Figure 13:
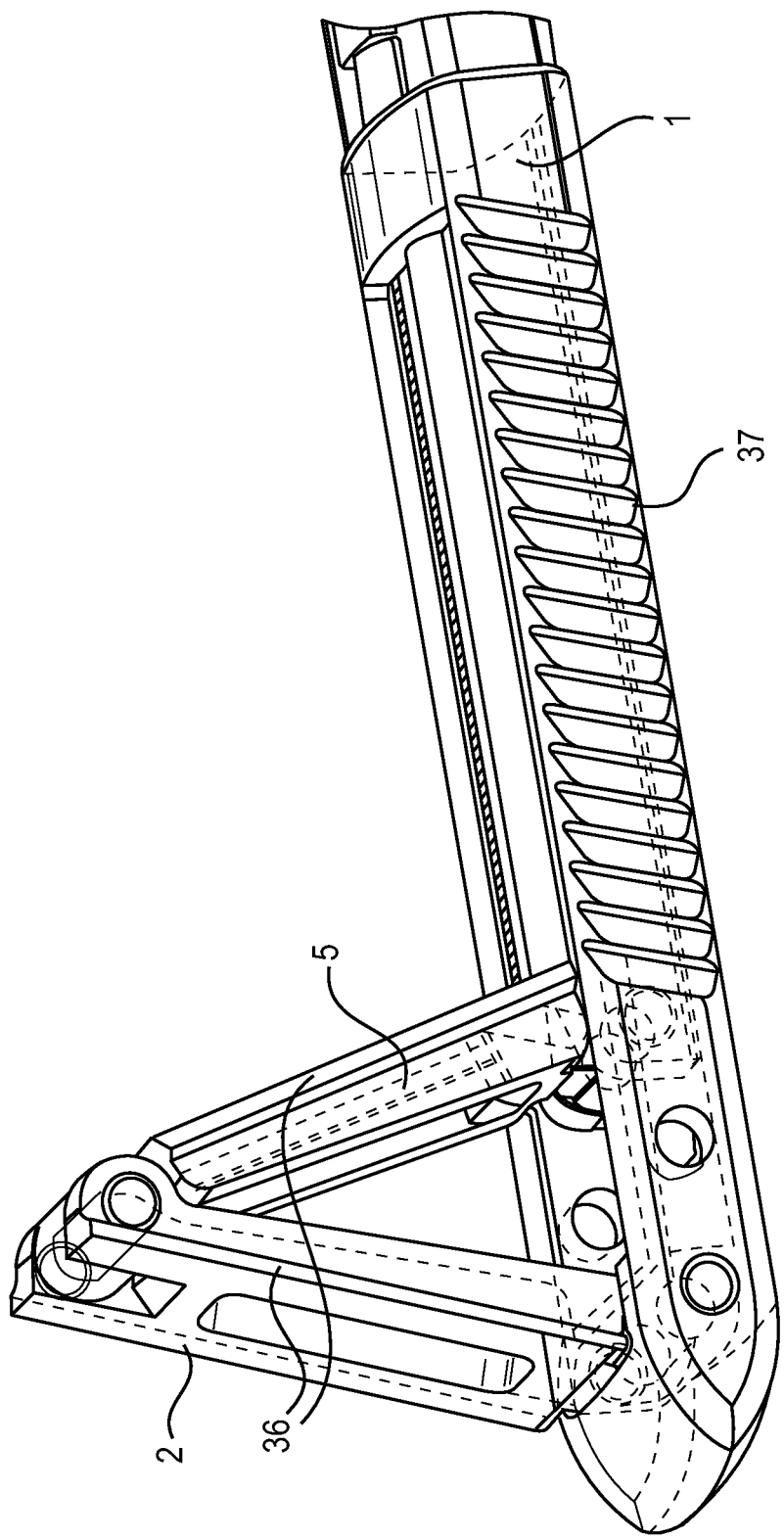
FIG. 13 is a schematic diagram of a perspective view of the tip portion of a device for preparation of surgical sites, and in particular, vertebral members, according to an alternative embodiment.

In one embodiment, FIG. 13 illustrates A-frame members 2 and 5 having straight scraping edges 36 and a tip portion of cannula 1 having rasp teeth 37 on the narrow edge of the cannula 1.

In embodiments, file teeth may be added to the narrow edges of device 100 to facilitate limited bone removal at the rim of a vertebral endplate. This ensures that the endplates remain parallel even though the device may be primarily distracting the opening from one side. In addition, the filed groove may ensure that an instrument deploying a spinal implant registers in the exact location at the posterior edge of the disc opening. Additionally, as shown in FIG. 4, for example, large openings 38 in the A-frame members 2 and 5 may allow disc tissue to exit from within the A-frame members, to avoid jamming the A-frame members and preventing full retraction of the A-frame members 2 and 5 to a flat position. A cleanout port (e.g., port 97 in FIG. 1.4) may allow for flushing of the device 100 prior to sterilization for reuse.

In embodiments used for sizing, a surgeon may start with a smaller device 100 (width of the device or height of the disc space) to check the discectomy void. If the fit is loose, the surgeon may move up to the next size. The fully deployed height of the A-frame members 2 and 5 may be incrementally increased to size the discectomy void and/or to adjust the reach of any rasp or scraper features provided on the device. There may also be various sizes of the A-frame. In embodiments, the fully deployed height of the retractable members may correspond in size to the spinal implant to be implanted and the deployment instrument to be used to implant the spinal implant, so that the void is correctly sized.

In embodiments, device 100 may be rapidly removed by depressing the lock button 7 and pulling back on the actuator handle 14. The pitch of the threads on the rod may be changed to adjust the effect of the turns of the actuator handle 14.

In embodiments, device 100 may also be used as a distraction instrument. For example, device 100 may be inserted into a disc space through an annulotomy with the A-frame members facing a first vertebra endplate, and instead of then rotating the instrument 90 degrees for sizing or rasping purposes, the device 100 would remain oriented with the A-frame members facing the first vertebra endplate and the opposite side of the tip portion of the device 100 facing a second vertebra endplate. The device 100 would then be actuated to raise the A-frame members 2 and 5, which would then push the first vertebra endplate as the opposite side of the tip portion of the device 100 pushes the second vertebra endplate. As the A-frame members 2 and 5 rise, the device 100 would cause distraction in the disc space.

In embodiments, one or both of the A-frame members 2 and 5 may have a contact surface at their adjoining ends so that during distraction the members provide more distributed contact with a vertebra endplate, rather than contact by a corner of the members. For example, referring to FIGS. 5-7, the proximal end 71 of member 2 may have a rounded or flattened contour, rather than the corner edge shown in those figures. Such a contoured contact surface may provide better contact with a vertebra endplate and may allow sliding of a member against the vertebra endplate with less resistance.

In embodiments, device 100 may be used in vertebral bodies in a manner similar to that described above to achieve the same results except for the intervertebral space.

In embodiments, device 100 may have different configurations depending on the desired functions. For example, device 100 may have smooth edges on the A-frame members 2 and 5 to check the size and clearance of a discectomy void. As another example, device 100 may have sharpened edges or file teeth on the A-frame members 2 and 5 and file teeth on the narrow edges of the body of the instrument to use the device as a rasp or scraper to facilitate the cleanout of a disc space. As another example, the A-frame members 2 and 5 may have curved cutting edges to better match the shape of an annulus, such as an oval shape, and to permit the clearing of tissue as close to the edge of the annulus as possible. An embodiment of curved edges is shown and described below in reference to FIGS. 20.1-20.3. As another example, device 100 may have a cannula with a rasp surface or a smooth surface and A-frame members with a rasp surface or a smooth surface.

Embodiments of a device for preparation of surgical sites (e.g., preparation of vertebral members) may include provisions for accommodating varying anatomies or other structural conditions in which a device is used, which may depend on the particular surgical site of a patient. Examples of such variations may include the size and shape of an annulotomy through which a device is inserted and the size and shape of an intervertebral space in which a device is used. Embodiments may therefore provide varying configurations of extending and retracting members of a tool. As shown in FIGS. 4-7 for example, an embodiment of a tool may provide A-frame members 2 and 5 of a tool 21, which are each attached at their ends to each other at pivot pin 9B. Other embodiments may link the extending and retracting members of a tool in different configurations, e.g., suitable for different structural conditions or operational objectives, such as sizing or rasping. For example, instead of attaching the extending and retracting members at their ends, other embodiments may attach a first member to an intermediate portion of a second member, so that a portion of the second member extends beyond the attachment point.

As shown in FIGS. 15.1-15.3, an alternative embodiment provides a device 200 for preparation of surgical sites, and in particular, vertebral members, having a tool 221 with a distal member 202 and a proximal member 205. A proximal side of slide connector 4 may be connected to a distal side of an actuator rod, while a distal side of the slide connector 4 may be pivotably connected to a proximal side of the proximal member 205 by a pivot pin. A distal side of the proximal member 205 may be pivotably connected to an intermediate portion of distal member 202 by a pivot pin 9B. A distal side of distal member 202 may be connected to the cannula 1 by a pivot pin 8. The pivotable connections associated with the tool 221 may allow the tool 221 to extend from, and retract into, an opening 28 in the cannula 1 at the tip portion 19 of the device 200, as the slide connector 4 is moved distally and proximally by the actuator rod of the actuator assembly.

As shown in FIGS. 15.2 and 15.3, attaching proximal member 205 to an intermediate portion of distal member 202 may provide an extending portion 299 of distal member 202. The attachment point at pivot pin 9B may be positioned at any intermediate location as appropriate for a particular application. In the embodiment of FIGS. 15.1-15.3, the intermediate location is approximately at a midpoint of the distal member 202. Other intermediate locations are possible, however, and may depend on factors such as the desired length of the extending portion 299 and the ability to pivot the distal member 202 outward as the proximal member 205 is forced distally in the longitudinal direction, thereby pushing the distal member 202 at the pivot pin 9B to move the distal member 202 outward.

Providing an extending portion may allow a slim profile for a tool in the fully deployed condition. The slim profile may allow a user to conveniently maneuver a device within a surgical site, and may provide enhanced control and feel when measuring the size of the disc space or when removing bone or tissue with the device. For example, as shown in FIG. 15.3, once the device 200 is deployed within an implantation site, the cannula 1 can be moved back and forth in the longitudinal direction, as well as pivoted about the tip of the cannula 1, to move the distal member 202 within the implantation site, and to move the extending portion 299 both longitudinally and pivotally. Distal member 202 may include cutting edges 236 that may be used to cut bone or tissue as the device 200 is moved. Proximal member 205 may also include cutting edges 236.

Since the extending portion 299 causes the distal member 202 and the proximal member 205 to overlap in the retracted position, embodiments may include provisions for allowing the members 202 and 205 to lie flush with each other and with the outer surface of the cannula 1. An example of a retracted, flush configuration is shown in FIG. 15.1. To allow such a configuration, as shown in FIG. 15.2, an embodiment provides a recessed portion 297 of proximal member 205 that receives an end portion 295 of distal member 202. Likewise, distal member 202 may include a recessed portion 293 that receives an end portion 291 of proximal member 205. As shown in FIG. 15.1, in the retracted position, the recessed portions 293 and 297 allow the proximal member 205 and the distal member 202 to overlap each other, nest within each other, and assume a generally straight, longitudinal configuration, with the outer surface 289 of the proximal member 205, the outer surface 287 of the distal member 202, and the outer surface 285 of the cannula 1 generally flush with each other. That flush configuration may allow convenient insertion into a small incision or annulotomy, and may avoid catching on or damaging surrounding tissue.

Another embodiment for accommodating varying structural conditions of a site may provide an extending portion on a proximal member of a retractable tool. As shown in FIGS. 16.1-16.3, an embodiment provides a device 300 for preparation of surgical sites, and in particular, vertebral members, having a retractable tool 321 with a distal member 302 and a proximal member 305. A proximal side of slide connector 4 may be connected to a distal side of an actuator rod, while a distal side of the slide connector 4 may be pivotably connected to a proximal side of the proximal member 305 by a pivot pin. An intermediate portion of the proximal member 305 may be pivotably connected to a proximal side of distal member 302 by a pivot pin 9B. A distal side of distal member 302 may be connected to the cannula 1 by a pivot pin 8. The pivotable connections associated with the tool 321 may allow the tool 321 to extend from, and retract into, an opening 28 in the cannula 1 at the tip portion 19 of the device 300, as the slide connector 4 is moved distally and proximally by the actuator rod of the actuator assembly.

As shown in FIGS. 16.2 and 16.3, attaching distal member 302 to an intermediate portion of proximal member 305 may provide an extending portion 399 of proximal member 305. The attachment point at pivot pin 9B may be positioned at any intermediate location as appropriate for a particular application. In the embodiment of FIGS. 16.1-16.3, the intermediate location is approximately at a midpoint of the proximal member 305. Other intermediate locations are possible, however, and may depend on factors such as the desired length of the extending portion 399 and the ability to pivot the proximal member 305 outward as the proximal member 305 is forced distally in the longitudinal direction, thereby pushing the distal member 302 at the pivot pin 9B to move the distal member 302 and the proximal member 305 outward.

As with the previous embodiment, providing an extending portion may allow a slim profile for a tool in the fully deployed condition. The slim profile may allow a user to conveniently maneuver a device within a surgical site, and may provide enhanced control and feel when measuring the size of the disc space or when removing bone or tissue with the device. For example, as shown in FIG. 16.3, once the device 300 is deployed within an implantation site, the cannula 1 can be moved back and forth in the longitudinal direction, as well as pivoted about the tip of the cannula 1, to move the distal member 302 within the implantation site, and to move the extending portion 399 both longitudinally and pivotally. Proximal member 305 may include cutting edges 336 that may be used to cut bone or tissue as the device 300 is moved. Distal member 302 may also include cutting edges.

Since the extending portion 399 causes the proximal member 305 and the distal member 302 to overlap in the retracted position, embodiments may include provisions for allowing the members 302 and 305 to lie flush with, or below, the outer surface of the cannula 1. An example of a retracted, flush configuration is shown in FIG. 16.1. To allow such a configuration, as shown in FIG. 16.2, an embodiment provides a recessed portion 397 of proximal member 305 that receives an end portion 395 of distal member 302. Likewise, distal member 302 may include a recessed portion 393 that receives an end portion 391 of proximal member 305. As shown in FIG. 16.1, in the retracted position, the recessed portions 393 and 397 allow the proximal member 305 and the distal member 302 to overlap each other, nest within each other, and assume a generally straight, longitudinal configuration, with the outer surface 389 of the proximal member 305 generally flush with the outer surface 385 of the cannula 1, and with the outer surface 387 of the distal member 302 recessed below the outer surface 385 of the cannula 1 and the outer surface 389 of the proximal member 305. That flush and recessed configuration may allow convenient insertion into a small incision or annulotomy, and may avoid catching on or damaging surrounding tissue.

Another embodiment for accommodating varying structural conditions of a surgical site may provide a specially shaped or contoured retractable member of a tool, to match the shape of a surgical site (e.g., an annulus) in which a device is inserted. Matching the shape may allow the retractable member to be positioned closer to, or even in substantially full contact with, a perimeter wall of the surgical site. The matching contours may allow the tool to provide a more accurate measurement of the surgical site and a more complete reach to cut or otherwise clear bone or tissue from the site. As an example, a specially shaped edge and/or outer surface of a retractable member may be curved to match a portion of an oval-shaped annulus. Other shapes and contours, such as triangular or other polygonal shapes, are possible, depending on the shapes of the anatomical structures for which the tool is intended.

As an example, as shown in FIGS. 20.1-20.3, an embodiment may provide a device 400 for preparation of surgical sites, and in particular, vertebral members, having a tool 421 with a distal member 402 and a proximal member 405. Device 400 and tool 421 may be similar in many respects to device 200 and tool 221 of the embodiment of FIGS. 15.1-15.3, for example, in terms of the configurations and attachments of the retractable members of the tools. Those similarities would be apparent to the skilled artisan from the figures and description, and for conciseness, will not be described herein. Device 400 differs from device 200 in aspects related to the shapes of the edges and outer surfaces of the retractable members. In particular, as shown in FIGS. 20.1-20.3, distal member 402 may have curved lateral edges 436 and a curved outer surface 437, which may correspond to the curve of a perimeter wall of a surgical site, such as a curved perimeter wall of an annulus. As shown in the fully deployed position of FIG. 20.3, the complementary shapes between the tool 421 and a perimeter wall of a surgical site may allow the outer surface 437 to be positioned near, or in substantial contact with, the wall, so that the tool 421 may accurately measure the size of the site or may clear tissue or bone from the site starting close to the wall and using the curved lateral edges 436 for cutting.

Figure 21:
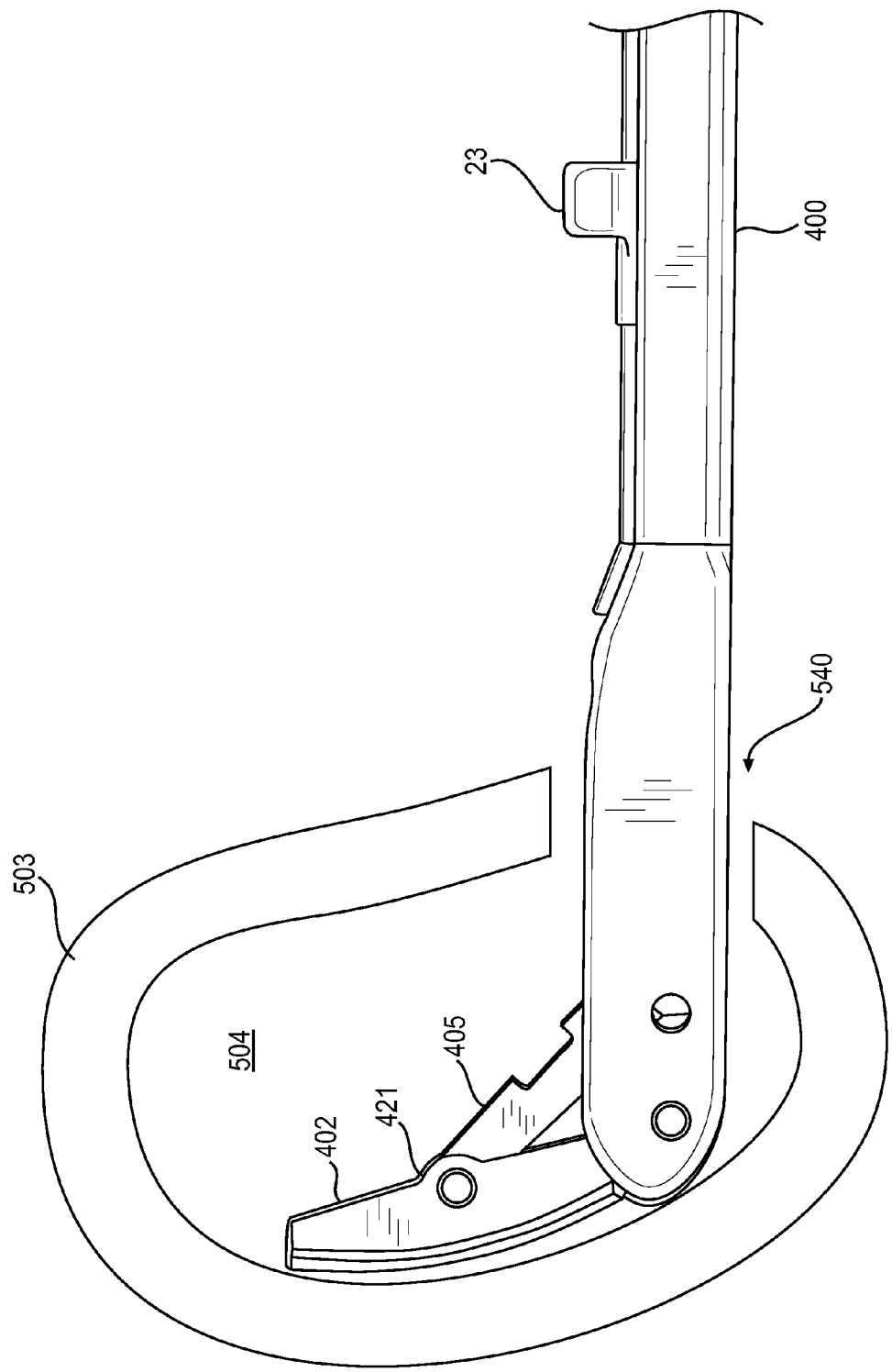
FIG. 21 is a schematic diagram illustrating an embodiment of a method for preparation of surgical sites, and in particular, vertebral members, using the device of FIG. 20.1.

As an example, referring to FIG. 21, in sizing or clearing a surgical or implantation site, device 400 may be inserted into an annulotomy 540 of an annulus 503 and actuated to the fully deployed position of FIG. 20.3, after which the entire device 400 may be moved longitudinally (generally left and right in FIG. 21) or may be moved pivotally around the tip of the cannula 1, within the disc space 504 of the annulus 503. Alternatively, the cannula 1 may be maintained at a substantially fixed position, and the tool 421 may be extended and retracted moving back and forth between the fully retracted position of FIG. 20.1 and the fully extended position of FIG. 20.3. As the tool 421 moves between those end positions, distal member 402 may confirm a clear opening within the site (e.g., the disc space 504 in FIG. 21) equal to the volume in which the distal member 402 pivots and, in addition, may clear tissue and bone from the site as the distal member 402 moves within the site and the lateral edges 436 scrape the tissue and bone.

In further embodiments, specially shaped edges and/or outer surfaces may be provided on the proximal member 305 of the device 300 of FIGS. 16.1-16.3 and on one or both of the proximal member 5 and distal member 2 of the device 100 of FIGS. 1.1-1.4.

Embodiments provide methods for the preparation of surgical sites, and in particular, vertebral members, using the devices disclosed herein. In an embodiment, a tip portion of a surgical site preparation device is inserted through an annulotomy until at least a portion of the retractable tool of the device is within the annulus. Optionally, if necessary, the device may be rotated after insertion to face the retractable tool in a desired extension direction. For example, for sizing or clearing an annulus, the device may be rotated such that the retractable tool faces in a horizontal direction between the vertebral endplates. In another example, for distracting, the device may be rotated such that the retractable tool faces in a vertical direction facing a vertebral endplate. The device may also be rotated to the desired orientation and then inserted into the annulotomy.

After the retractable tool is facing the desired extension direction, the retractable tool is then actuated so that the retractable members of the retractable tool extend laterally away from the tip portion of the device, from an initial retracted position to a fully extended position. That movement of the retractable members may be used to indicate clearance within disc space of the annulus and to indicate the size and shape of the disc space. That movement may also be used to clear bone and tissue from the disc space to provide a desired clearance, size, or shape of the disc space. Alternatively, or in addition, once the retractable tool is in the fully extended position, the entire device may be moved to move the retractable members of the retractable tool within the annulus, to size the disc space within the annulus or to clear bone or tissue from within the annulus. The device may be moved longitudinally back and forth, may be pivoted about the tip portion of the device, or may be moved in combinations of movement thereof.

Figure 17:
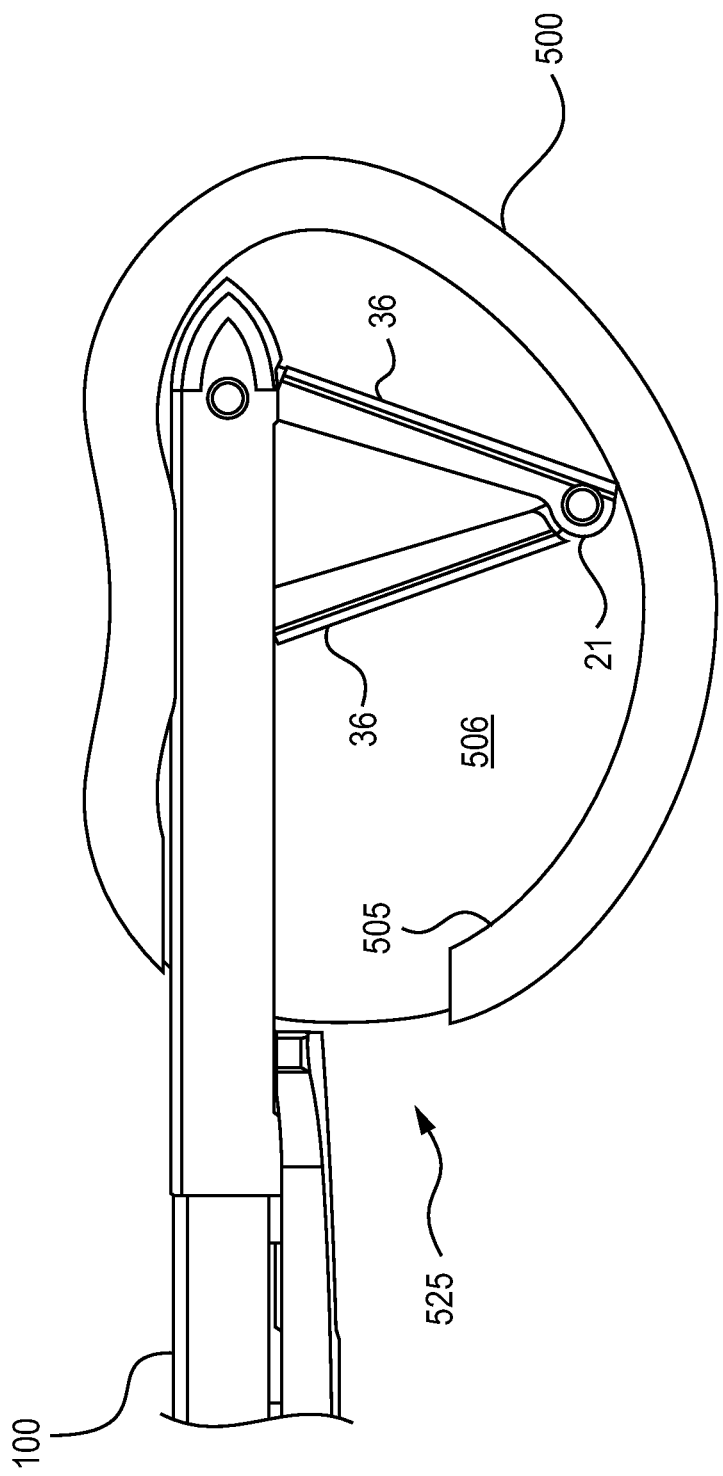
FIG. 17 is a schematic diagram illustrating an embodiment of a method for preparation of surgical sites, and in particular, vertebral members, using the device of FIG. 1.1.

FIGS. 17-19.2 and 21 illustrate embodiments of methods for the preparation of surgical sites, and in particular, vertebral members, using the devices disclosed herein. FIG. 21 is described above. FIG. 17 illustrates an embodiment of the device 100 of FIG. 1.1 inserted through an annulotomy 525 and into an annulus 500, with the retractable tool 21 in a partially extended position, in between the fully retracted and the fully extended positions. As shown, the device 100 may contact the inner perimeter walls 505 of the annulus 500 to provide indications of the size and shape of the disc space 506 of the annulus 500. As an example, if the retractable tool 21 contacts a wall 505 of the annulus 500 such that further deployment of the tool 21 is hindered or prevented, then a user may determine that the disc space 506 is not sufficiently large (cleared) to receive an implant of a certain size corresponding to the fully deployed tool 21. A user may then use the device 100 to increase the size of the annulus 500, by using rasp teeth (not shown) on the cannula 1 of the device 100 and/or scraping edges 36 of the tool 21.

FIGS. 18.1-18.4 illustrate an embodiment of the device 200 of FIG. 15.1 being deployed in an annulus 501. As shown in FIG. 18.1, the tip portion of device 200 is first inserted through an annulotomy 526 and into an annulus 501. The tip portion of the device 200 may be positioned at a longitudinal end of the annulus 501 with the extension direction of the retractable tool 221 generally facing the interior of the annulus in a direction parallel to the faces of the opposing vertebral endplates. Optionally, the device 200 first could be inserted through the annulotomy 526 with the extension direction of the retractable tool 221 generally facing in a direction perpendicular to the faces of the opposing vertebral endplates, and once inserted, may be rotated approximately 90 degrees to the position shown in FIG. 18.1.

With at least a portion of the retractable tool 221 inside the disc space 507 of the annulus 501, the retractable tool 221 may then be actuated so that the proximal member 205 and distal member 202 extend out of the opening 28 in the cannula 1, as shown in the partially extended position of FIG. 18.2. For clarity and illustration purposes, FIGS. 18.2-18.4 show the annulus 501 in dashed lines. In the embodiment of FIG. 18.2, the proximal member 205 is sliding through the annulotomy 526 and simultaneously extending out of the opening 28, while the distal member 202 is extending out of the opening 28 and pivoting around pivot pin 8 within the disc space 507 of the annulus 501. During this pivoting motion, the distal member 202 may be used to cut bone or tissue, using for example the cutting edges 236. Pieces of cut bone or tissue may pass through the opening 293 in distal member 202 to help move the loose bone and tissue toward the annulotomy 526 and out of the annulus 501. The pivoting motion of distal member 202 may also be used to confirm clearance through the disc space 507 of the annulus 501, for receiving a correspondingly sized implant.

The retractable tool 221 may be further actuated so that the proximal member 205 and the distal member 202 reach their fully extended positions, as shown in FIG. 18.3. The device 200 may be locked at this point to secure the proximal member 205 and the distal member 202 at their fully extended positions. Then, as described in embodiments above, the entire device 200 may be moved to measure the size and shape of the disc space 507 of the annulus 501 using the retractable tool 221, and to cut bone and tissue to clear the disc space 507 of the annulus 501 for insertion of a correspondingly sized implant. As an example, FIG. 18.4 illustrates a correspondingly sized implant 527 (shown in dashed lines for clarity and illustration purposes) positioned within the disc space 507 of the annulus 501 and within the pivoting arc of the distal member 202. Implant 527 may be a coiled implant as shown. Other types of implants are also possible.

After the disc space 507 of the annulus 501 is sized and, if necessary, cut, the retractable tool 221 of the device 200 may be retracted so that the proximal member 205 and the distal member 202 return to their initial retracted positions, lying flat within the opening 28 as shown in FIG. 18.1. The device 200 may then be withdrawn through the annulotomy 526 and out of the annulus 501. The implant 527 may then be inserted using an implantation device, for example, as disclosed in U.S. Pat. No. 7,922,767 to Sack et al., issued Apr. 12, 2011, and U.S. Pat. No. 8,197,548 to Sack et al., issued Jun. 12, 2012, both of which are herein incorporated by reference in their entirety.

Another embodiment of a method for the preparation of surgical sites, and in particular, vertebral members, is shown in FIGS. 19.1-19.2. FIGS. 19.1-19.2 illustrate an embodiment of the device 300 of FIG. 16.1 inserted through an annulotomy 528 and into disc space 509 of an annulus 502, with the retractable tool 321 in a fully extended position. In reaching the fully extended position, the proximal member 305 of retractable tool 321 may slide under an edge of the annulotomy 528 as the proximal member 305 extends outward from the opening 28. As the proximal member 305 is extending, the device 300 may contact the inner perimeter walls 529 of the annulus 502 to provide indications of the size and shape of the disc space 509 of the annulus 502. As an example, if the retractable tool 321 contacts a wall 529 of the annulus 502 such that further deployment of the tool 321 is hindered or prevented, then a user may determine that the disc space 509 of the annulus 502 is not sufficiently large (cleared) to receive an implant of a certain size corresponding to the fully deployed tool 321. A user may then use the device 300 to increase the size of the disc space 509 of the annulus 502, by using scraping edges 336 of the tool 321. In embodiments, a surgeon may start with a smaller size instrument and work up to larger sizes.

Once the retractable tool 321 is in the fully extended position, the device 300 may be locked to keep the tool 321 in that position. As described in embodiments above, the entire device 300 may then be moved to move the retractable tool 321 within the annulus 502, for example, to measure the cleared disc space 509 in the annulus 502 or to cut and clear bone and tissue from the disc space 509 within the annulus 502. Proximal member 305 and distal member 302 may define openings, such as opening 394 in FIG. 19.1, to allow cut pieces of bone and tissue to pass through and around the retractable tool 321 and out of the annulus 502 through the annulotomy 528. The retractable tool 321 may be used to size and/or cut the disc space 509 within the annulus 502 for insertion of a correspondingly sized implant. As an example, FIG. 19.2 illustrates a correspondingly sized implant 537 (shown in dashed lines for clarity and illustration purposes) positioned within the annulus 502. A user may determine that the implant 537 will fit within the disc space 509 of the annulus 502 by either pivoting the proximal member 305 through the volume represented by the dashed implant 537 in FIG. 19.2 or by moving (e.g., pushing and/or pulling) the entire device 300 in a longitudinal direction (generally right to left in FIG. 19.2) to move the retractable tool 321 from one longitudinal wall 529A of the annulus 502 to the opposite longitudinal wall 529B of the annulus 502. Implant 537 may be a coiled implant as shown. Other types of implants are also possible. In embodiments, different types of instruments can be used in any combination with other types of instruments to create and/or size a desired discectomy disc space.

Embodiments of a surgical site preparation device may have several different uses. For example, device 100 of FIG. 1.1 may be used in a disc space to size a discectomy void/3D void for an implant. As another example, a device 100 may be used in a disc space as a rasp or scraper to help perform a discectomy. As another example, a device 100 may be used as a final discectomy preparation tool to prepare the vertebral bodies to create bone bleeding in preparation for the intervertebral body fusion device. As another example, a device 100 may be used in a disc space as a distractor and to correct deformity. As another example, a device 100 may be used in a vertebral body to create a void. As another example, a device 100 may be used in a vertebral body to increase the height of the vertebral body. In another example, a device 100 may be used in a compression fracture of a vertebra to reduce the fracture including vertebral height restoration.

In embodiments, an instrument for preparing surgical sites, and in particular, vertebral members, may be sized and configured similarly to an instrument for deploying an implant so that a doctor may become quickly accustomed to the operation of the preparation instrument. The similar constructions may also allow common parts for ease of manufacture and cost reduction.

Although embodiments disclosed herein may have been described in the context of vertebral members, one of ordinary skill in the art would appreciate that the disclosed devices and methods could be used for other surgical applications including, for example, the distraction of bones for purposes of orthopedic surgery. Accordingly, notwithstanding the particular benefits associated with the use of the devices and methods with vertebral members, the present embodiments should be considered broadly applicable to any surgical site that could benefit from, for example, sizing, clearing, or distraction.

The foregoing disclosure of the preferred embodiments has been presented for purposes of illustration and description. It is not intended to be exhaustive or to limit the present embodiments to the precise forms disclosed. Many variations and modifications of the embodiments described herein will be apparent to one of ordinary skill in the art in light of the above disclosure.

While various embodiments have been described, the description is intended to be exemplary, rather than limiting and it will be apparent to those of ordinary skill in the art that many more embodiments and implementations are possible. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the present embodiments are not to be restricted except in light of the attached claims and their equivalents. Also, various modifications and changes may be made within the scope of the attached claims.

Further, in describing representative embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the present embodiments.

What is claimed is:

1. A device for preparing a surgical site comprising:
a retractable tool; and
an actuator connected to the retractable tool,
wherein the retractable tool comprises a distal member and a proximal member,
wherein a distal side of the distal member is fixed in a longitudinal direction and pivotable at a point of rotation,
wherein a proximal side of the proximal member is pivotably connected to the actuator,
wherein in a retracted position the distal member is pivotably connected to the proximal member at a pivot axis longitudinally in between the point of rotation and the proximal side of the proximal member,
wherein in the retracted position the distal member and the proximal member extend generally along the longitudinal direction,
wherein, from the retracted position, moving the actuator in a distal direction pushes the proximal member and the distal member such that the proximal member pivots with respect to the actuator and the distal member, the distal member pivots with respect to the proximal member and the point of rotation, and the proximal member and the distal member move laterally outward with respect to the longitudinal direction toward an extended position, and
wherein at least one of the distal member and the proximal member defines a through-opening that extends transverse to the longitudinal direction and allows passage of bone and tissue when the proximal member and the distal member move laterally inward from the extended position to the retracted position.

2. The device of claim 1, wherein the actuator comprises:
an actuator rod; and
an actuator handle,
wherein a distal end of the actuator rod is connected to the proximal side of the proximal member, and
wherein a proximal end of the actuator rod is connected to the actuator handle.

3. The device of claim 2, wherein the actuator handle is longitudinally and rotationally fixed to the actuator rod, wherein the actuator rod is connected to the proximal member of the retractable tool by a threaded connection, and wherein rotation of the actuator handle rotates the actuator rod and adjusts the distance between the actuator handle and the proximal member.

4. The device of claim 3, further comprising a locking mechanism that prevents movement of the actuator rod in the longitudinal direction but allows rotational movement of the actuator rod.

5. The device of claim 4, wherein the locking mechanism comprises:
   at least one of annular ribs and annular grooves on the actuator rod; and
   a button having at least one of annular ribs and annular grooves that engage and disengage the at least one of annular ribs and annular grooves of the actuator rod.

6. The device of claim 2, further comprising a cannula, wherein the actuator rod is disposed within the cannula, wherein the cannula defines an opening at a tip portion of the device,
   wherein the proximal member and the distal member are disposed within the opening when in the retracted position,
   wherein the distal side of the distal member is pivotably connected to the cannula at a distal end of the opening, and
   wherein the proximal member and the distal member extend out of the opening when the actuator rod moves in the distal direction.

7. The device of claim 6, wherein in the retracted position, an outer surface of the proximal member, an outer surface of the distal member, and an outer surface of the cannula around the opening are generally flush with each other.

8. The device of claim 6, further comprising a fixed handle on a proximal side of the cannula, wherein travel of the actuator handle in a distal direction is limited by contacting the fixed handle.

9. The device of claim 1, wherein at least one of the proximal member and the distal member has a first longitudinal cutting edge and a second longitudinal cutting edge opposite to the first longitudinal cutting edge, and wherein in the extended position the first and second longitudinal cutting edges protrude in directions generally parallel to the pivot axis.

10. The device of claim 1, further comprising a depth gauge assembly.

11. The device of claim 1, wherein the device may be used for sizing, surface preparation, or distraction.

12. The device of claim 1, wherein a proximal end of the distal member is pivotably connected to a distal end of the proximal member.

13. The device of claim 1, wherein a distal end of the proximal member is pivotably connected to an intermediate portion of the distal member,
   wherein, in the retracted position, an extension portion of the distal member extends beyond the distal end of the proximal member toward the proximal side of the proximal member, and overlaps the proximal member.

14. The device of claim 13, wherein the proximal member defines a recessed portion for receiving the extension portion of the distal member so that an outer surface of the distal member and an outer surface of the proximal member are substantially flush when in the retracted position.

15. The device of claim 13, wherein the distal member defines a recessed portion for receiving the extension portion of the proximal member so that an outer surface of the proximal member and an outer surface of the distal member are substantially flush when in the retracted position.

16. The device of claim 1, wherein a proximal end of the distal member is pivotably connected to an intermediate portion of the proximal member,
   wherein, in the retracted position, an extension portion of the proximal member extends beyond the proximal end of the distal member toward the distal side of the distal member, and overlaps the distal member.

17. The device of claim 1, wherein at least one of the proximal member and the distal member is curved to match a shape of a curved perimeter wall of a vertebral disc annulus.

18. A device for preparing a surgical site, the device extending from a proximal handle portion to a distal tip portion and defining a longitudinal axis, the device comprising:
   a cannula extending generally along the longitudinal axis and defining an opening at a distal portion of the cannula;
   a cannula handle fixed to a proximal portion of the cannula;
   an actuator rod disposed within the cannula and moveable within the cannula in a longitudinal direction generally along the longitudinal axis;
   an actuator handle that is attached to a proximal portion of the actuator rod and that is disposed proximal to the cannula handle;
   a distal member; and
   a proximal member,
   wherein a distal side of the distal member is pivotably connected at a first point to a distal portion of the cannula,
   wherein a proximal side of the proximal member is pivotably connected to the actuator rod at a second point,
   wherein in a retracted position the distal member is pivotably connected to the proximal member longitudinally in between the first point and the second point,
   wherein in the retracted position the distal member and the proximal member are disposed within the cannula at the opening and extend generally along the longitudinal direction, and
   wherein, from the retracted position, moving the actuator handle toward the cannula handle moves the actuator rod in a distal direction relative to the cannula to push the proximal member and the distal member such that the proximal member pivots with respect to the actuator rod and the distal member, the distal member pivots with respect to the proximal member and the first point, and the proximal member and the distal member move laterally out of the opening.

19. The device of claim 18, wherein the actuator handle is longitudinally and rotationally fixed to the actuator rod, wherein the actuator rod is connected to the proximal member by a longitudinally adjustable connection, and wherein rotation of the actuator handle rotates the actuator rod and adjusts the distance between the actuator handle and the proximal member.

20. The device of claim 18, further comprising a locking mechanism that, in an extended position of the distal member and the proximal member, prevents movement of the actuator rod in the longitudinal direction but allows rotational movement of the actuator rod.

21. A method for preparing a surgical site, the method comprising:
   inserting into the surgical site a device in a retracted position,
   wherein the device has a retractable tool and an actuator connected to the retractable tool,
   wherein the retractable tool comprises a distal member and a proximal member,
   wherein a distal side of the distal member is fixed in a longitudinal direction and pivotable at a point of rotation, wherein a proximal side of the proximal member is pivotably connected to the actuator, wherein in the retracted position the distal member is pivotably connected to the proximal member at a pivot axis longitudinally in between the point of rotation and the proximal side of the proximal member, and wherein in the retracted position the distal member and the proximal member extend generally along the longitudinal direction;

moving the actuator in a distal direction so that the actuator pushes the proximal member and the distal member such that the proximal member pivots with respect to the actuator and the distal member, the distal member pivots with respect to the proximal member and the point of rotation, and the proximal member and the distal member move laterally outward with respect to the longitudinal direction and across the surgical site into an extended position, wherein at least one of the distal member and the proximal member has a first longitudinal cutting edge and a second longitudinal cutting edge opposite to the first longitudinal cutting edge, wherein in the extended position the first and second longitudinal cutting edges protrude in directions generally parallel to the pivot axis; and moving the device so that the first longitudinal cutting edge cuts a first bone or tissue surface and the second longitudinal cutting edge cuts a second bone or tissue surface opposite to the first bone or tissue surface.

22. The method of claim 21, further comprising sizing the surgical site using the extended proximal member and the extended distal member.

23. The method of claim 21, wherein both of the at least one of the distal member and the proximal member have a first longitudinal cutting edge and a second longitudinal cutting edge and the method further comprises cutting the surgical site using both of the at least one of distal member and the proximal member.

24. The method of claim 21, further comprising distracting the surgical site using the extended proximal member and the extended distal member.

25. The method of claim 21, locking the actuator to prevent longitudinal movement of the actuator when the proximal member and the distal member are in a fully extended position, and moving the device such that the fully extended proximal member and the fully extended distal member move within the surgical site.

26. The method of claim 21, further comprising moving the actuator in a proximal direction so that the actuator pulls the proximal member and the distal member such that the proximal member pivots with respect to the actuator and the distal member, the distal member pivots with respect to the proximal member and the point of rotation, and the proximal member and the distal member move laterally inward with respect to the longitudinal direction to the retracted position.

* * * * *